United States Patent [19]

Funk et al.

[11] Patent Number: 5,710,247
[45] Date of Patent: Jan. 20, 1998

[54] PROCESS AND INTERMEDIATES FOR THE SYNTHESIS OF LHRH ANTAGONISTS

[75] Inventors: Kenneth W. Funk, Lindenhurst; Edwin O. Lundell; Robert B. Miller, both of Libertyville; Jane L. Chang, Buffalo Grove; Vimal Kishore, Mundelein; James J. Napier, Lindenhurst, all of Ill.; Michael A. Staeger, Greenfield, Wis.

[73] Assignee: Abbott Laboratories, Abbott Park, Ill.

[21] Appl. No.: 618,674

[22] Filed: Mar. 19, 1996

[51] Int. Cl.$^6$ ............................ A61K 38/04; C07K 4/00; C07K 1/02

[52] U.S. Cl. .................. 530/327; 530/328; 530/330; 530/331; 530/333; 530/338; 530/339; 562/562; 562/575

[58] Field of Search .................... 530/327, 328, 530/330, 331, 333, 338, 339; 562/562, 575

[56] References Cited

U.S. PATENT DOCUMENTS

| | | | |
|---|---|---|---|
| 5,110,904 | 5/1992 | Haviv et al. | 530/313 |
| 5,502,035 | 3/1996 | Haviv et al. | 514/15 |

FOREIGN PATENT DOCUMENTS

| | | | |
|---|---|---|---|
| 9413313 A | 6/1994 | WIPO | . |

OTHER PUBLICATIONS

Methods Neurosciences, vol. 34 (1993), pp. 3–18, F. Haviv et al., "Synthetic Approaches to Incorporation of Novel Amino Acids in to Gonadotropin Releasing Hormone Peptides".

Int. J. Peptide & Protein Research, vol. 41, No. 4 (1993), pp. 342–346, H. B. Arzen et al., "Temporary Serine Protection in Solid Phase Synthesis of LHRH Analogs".

J. Peptide Science, vol. 1, No. 2 (1995), pp. 89–105, G.A. Flouret, et al., "Antiovulatory Antagonists of LHRH related to Antide".

*Primary Examiner*—Cecilia J. Tsang
*Assistant Examiner*—Bennett Celsa
*Attorney, Agent, or Firm*—Mona Anand

[57] ABSTRACT

A method is provided for preparing decapeptide and undecapeptide derivatives of LHRH by solution phase peptide chemistry as well as intermediate peptides useful in the same method.

18 Claims, No Drawings

1

PROCESS AND INTERMEDIATES FOR THE SYNTHESIS OF LHRH ANTAGONISTS

TECHNICAL FIELD

The present invention relates to a method of chemical synthesis and to organic compounds which are useful intermediates in that process. More particularly, the present invention relates to a method of synthesizing LHRH antagonist peptides and intermediate oligopeptides useful in that process.

BACKGROUND OF THE INVENTION

The gonadotropins: follicle stimulating hormone (FSH), luteinizing hormone (LH), and chorionic gonadotropin (CG), are required for ovulation, spermatogenesis, and the biosynthesis of sex steroids. A single hypothalamic hormone, gonadotropin-releasing hormone GnRH (also known as luteinizing hormone-releasing hormone, LHRH) is responsible for regulating the secretion of both FSH and LH in mammals.

The structure of LHRH was determined by A. V. Schally, et al., Science. 173:1036–1037 (1971). Early attempts to prepare peptides having LHRH-like activity centered on the synthesis of compounds which were LHRH agonists. However, in 1976 it was found that while individual doses of LHRH stimulated the release of gonadotropin, the continuous administration of small doses of LHRH or chronic administration of LHRH agonists had the opposite effect. This finding stimulated research for the discovery of both agonist and antagonist analogs of LHRH as agents useful for regulating sex steroids in mammals. A considerable number of patents and articles in the open literature disclose analogs of LHRH which either act as agonists of LHRH (i.e. act to stimulate the release of LH and FSH) or as antagonists of LHRH (i.e. act to inhibit the release of LH and FSH). For the most part, these compounds contain nine or ten aminoacyl residues, substituting naturally-occurring or non-naturally-occurring amino acid residues at one or more positions in the natural sequence of LHRH. In some cases, active antagonists of LHRH have been reported which contain fewer than nine amino acid residues.

The literature has reported that LHRH analogs are useful for the treatment of a variety of conditions in which the suppression of sex steroids plays a key role including contraception, delay of puberty, treatment of benign prostatic hyperplasia, palliative treatment or remission of hormonal-dependent tumors of the breast and ovaries, palliative treatment or remission of hormonal-dependent tumors of the prostate, the treatment of cryptoorchidism, hirsutim in women, gastric motility disorders, dysmenorrhea, and endometriosis.

Methodologies for preparing LHRH analogs have been previously described. The literature describes the stepwise synthesis of LHRH analogs using standard solid and solution phase peptide chemistry techniques. Solid phase peptide synthesis however is neither practical, efficient nor cost effective for the large scale production of commercially valuable LHRH analogs. Although solution phase chemistry is more cost effective (and therefore the method of choice for scaled up peptide production), this method can also be inefficient, time consuming and costly if the production process requires multiple purification steps. Thus there is a need for solution phase synthetic processes which allow a manufacturer to produce peptides in high yield, with a high degree of purity and in a timely and cost effective manner.

SUMMARY OF THE INVENTION

In general, the method of the present invention employs solution phase synthetic techniques to produce with a high degree of purity, the final product employing novel protected intermediate peptides having a length of 3–7 amino acids. In its principal aspect, the present invention comprises a process for preparing an LHRH antagonist having the structure Q-D-2Nal$^1$D-4ClPhe$^2$-D-3Pal$^3$-Ser$^4$-NMeTyr$^5$-D-Lys(Nic)$^6$-Leu$^7$-Lys(iPr)$^8$-Pro$^9$-D-Ala$^{10}$NH$_2$ wherein the process comprises the step of coupling a compound IV having the formula P$^1$-Ser(P$^2$)-NMeTyr(P$^3$)-D-Lys(Nic)-Leu-Lys(iPr)-Pro-D-AlaNH$_2$ wherein P$^1$ is an amino protecting group and P$^2$ and P$^3$ are —OH protecting groups with a compound III having the formula Q-D-2Nal-D-4ClPhe-D-3Pal-OH in which Q is either N-acetyl or THF-Gly. Under the coupling conditions described herein, the desired LHRH antagonist is produced directly (i.e. without the need for additional processing to remove any remaining protecting groups).

In another embodiment of the present invention, the process comprises the step of preparing compound IV by coupling a compound I having the formula P$^1$-aa$_1$-Lys(iPr)-Pro-D-AlaNH2 wherein aa$_1$ is absent or is Leu with a compound II having the formula P$^1$- Ser(P$^2$)-NMeTyr(P$^3$)-D-Lys(Nic)-aa$_1$-OH with the proviso that aa$_1$ is not simultaneously present in both compounds I and II.

In another embodiment of the present invention, the process comprises the step of preparing compound I from a compound A$_2$ having the formula P$^1$-aa$_1$-Lys(P$^5$)-Pro-D-AlaNH$_2$ wherein P$^5$ is an amino protecting group orthogonal to P$^1$.

In another embodiment of the present invention, the process comprises the step of reacting the dicyclohexylamine salt of tetrahydrofuroic acid with the p-toluenesulfonic acid salt of Gly-O-P$^4$ wherein P$^4$ is a carboxyl protecting group to form THF-Gly-OH. THF-Gly-OH is then reacted with other pre-intermediate compounds (defined below) in forming compound III.

In a further embodiment of the present invention, there are provided certain classes of optionally protected pre-intermediate oligopeptide compounds useful in the process of the invention. The compounds of the present invention include derivatized single amino acids as well as di-, tri-, tetra-, penta-, hexa- and heptapeptides useful in the solution phase synthesis of LHRH analogs.

DETAILED DESCRIPTION AND PREFERRED EMBODIMENTS

A. Definitions

For convenience in describing this invention, the conventional abbreviations for the various common amino acids are used as generally accepted in the peptide an as recommended by the IUPAC-IUB Commission on Biochemical Nomenclature, Biochemistry II, 1726, 1972. These represent L-amino acids with the exception of the achiral amino acid glycine, and with the further exception of any unnatural or natural amino acids which are achiral, or are otherwise designated as D-. All peptide sequences mentioned herein are written according to the generally accepted convention whereby the N-terminal amino acid is on the left and the C-terminal amino acid is on the right. Furthermore, the notation of "—O—P$^4$" on a C-terminal amino acyl residue in any of the formulae shown below indicates that the carboxyl function of the particular residue is esterified with a P$^4$ protecting group.

The compounds of the invention comprise asymmetrically substituted carbon atoms. The terms "S" and "R" configuration, as used herein, are as defined by the IUPAC 1974 Recommendations for Section E, Fundamental Stereochemistry, Pure Appl. Chem (1976) 45, 13–30.

Furthermore, as used herein, the designation "THF-Gly" refers to either the 2S or 2R configuration of THF-Gly and to racemic mixtures of THF-Gly (i.e. 2R,S-THF-Gly).

Other abbreviations which are useful in describing the invention are the following:

TABLE 1

Amino Acids and Tetrahydrofuroic acid

| Amino acids | Abbreviation |
|---|---|
| 3-(2-Naphthyl)—D—alanine | D—2Nal |
| 3-(4-Chlorophenyl)—D—alanine | D—4ClPhe |
| 3-(3-Pyridyl)—D—alanine | D—3Pal |
| N—Methyl—L—tyrosine | NMeTyr |
| $N^6$—Nicotinyl—D—lysine | D—Lys(Nic) |
| $N^6$—Isopropyl—L—lysine | Lys(iPr) |
| Tetrahydrofuroic acid | THFA |
| Tetrahydrofuroic acid dicyclohexylammonium salt | THFA.DCHA |

TABLE 2

Protecting Groups

| Protecting groups | Abbreviation |
|---|---|
| t-Butoxycarbonyl | Boc |
| Benzyloxycarbonyl | Cbz |
| 9-Fluorenylmethyloxycarbonyl | Fmoc |
| Methyl | Me |
| Ethyl | Et |
| Benzyl | Bzl |
| 2,6-Dichlorobenzyl | $Cl_2Bzl$ |
| Allyl | All |

TABLE 3

Reagents

| Reagent | Abbreviation |
|---|---|
| 1-(3-Dimethylaminopropyl)-3-ethylcarbodiimide hydrochloride | EDC.HCl or EDC |
| 1-Hydroxybenzotriazole hydrate | HOBt |
| 3-Hydroxy-1,2,3-benzotriazin-4(3H)-one | HOOBt |
| Trimethylsilyl trifluoromethanesulfonate | TMSOTf |
| 2,3,6-Trimethylphenol | TMP |
| p-Toluenesulfonic acid | TsOH or HOTs |
| Diisopropylethylamine | DIEA |
| N—Methylpyrrolidinone | NMP |
| N—Methylmorpholine | NMM |
| Trifluoroacetic acid | TFA |

B. Solution Phase Synthesis of Q-D-2Nal$^1$D-4ClPhe$^2$-D-3Pal$^3$-Ser$^4$-NMeTyr$^5$-D-Lys(Nic)$^6$-Leu$^7$-Lys(iPr)$^8$-Pro$^9$-D-Ala$^{10}$NH$_2$ The present invention provides processes for making LHRH antagonist compounds via solution phase peptide chemistry. The general process of making an LHRH antagonist compound having the formula Q-D-2Nal$^1$-D-4ClPhe$^2$-D-3Pal$^3$-Ser$^4$-NMeTyr$^5$-D-Lys(Nic)$^6$-Leu$^7$-Lys(iPr)$^8$-Pro9-D-Ala$^{10}$NH$_2$ wherein Q is selected from the group consisting of N-acetyl and THF-Gly comprises the step of coupling a protected intermediate oligopeptide compound having the formula $P^1$-Ser($P^2$)-NMeTyr($P^3$)-D-Lys(Nic)-Leu-Lys(iPr)-Pro-D-AlaNH$_2$ (IV)

wherein $P^1$ is an amino protecting group, and $P^2$ and $P^3$ are —OH protecting groups with an oligopeptide compound having the formula Q-D-2Nal-D-4ClPhe-D-3Pal-OH (III)

wherein Q is defined as above, to produce the LHRH antagonist.

The general process may further comprise the step of preparing intermediate compound IV from intermediate compounds I and II. Intermediate compounds I and II have the formulae $P^1$-aa$_1$-Lys(iPr)-Pro-D-AlaNH$_2$ (wherein aa$_1$ is either absent or is Leu) and $P^1$-Ser($P^2$)-NMeTyr($P^3$)-D-Lys(Nic)-aa$_1$-OH respectively. When compounds I and II are used in the process to form compound IV, aa$_1$ may not be simultaneously present in both compounds. The process may further comprise the steps of preparing intermediate compounds I, II and III from a variety of pre-intermediates (as will be discussed below). The following diagrammatic scheme (Scheme 1) represents the overall process.

SCHEME 1

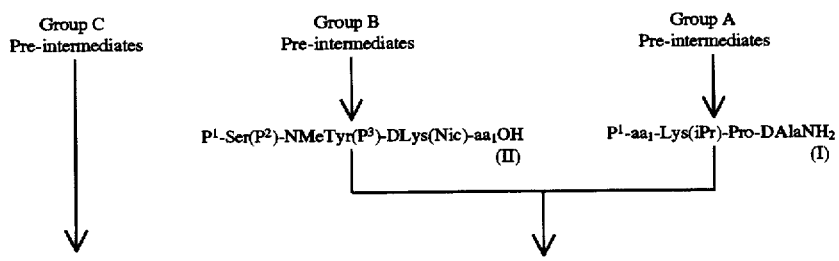

-continued
SCHEME 1

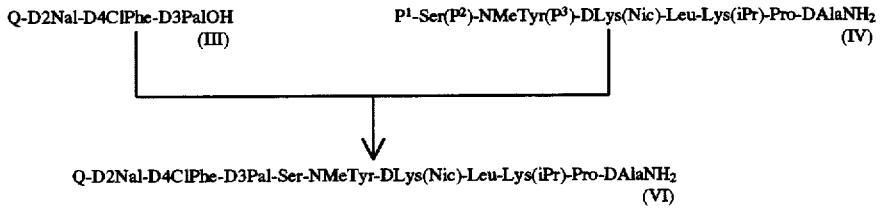

The general process of making the LHRH antagonist compounds is by coupling intermediate compound III with intermediate compound IV via convergent synthesis. "Convergent synthesis" as used herein refers to the process of coupling two or more peptides (of desired length) under conditions conducive to forming an amide linkage. For example, convergent synthesis may be used to couple (under conditions which eliminate or minimize racemization at chiral centers) a protected tripeptide with a properly protected tetrapeptide to form a heptapeptide. The heptapeptide may then be coupled to a second protected tetrapeptide to yield a desired undecapeptide, such as one of the LHRH antagonists described herein.

Generally, convergent coupling of intermediate compounds III and IV (or for that matter of intermediate compounds I and II) is performed using standard reagents and reaction conditions known to those of ordinary skill in the art; such reagents are listed in Table III above. (See eg. M. Bodansky, *Principles of Peptide Synthesis*, Springer-Verlag, Berlin, 2nd Edition, 1993). Of particular importance in the synthetic process is the manner and order of treating intermediate compounds III and IV to effect formation of the final product. In the principle aspect, compound IV is first treated with a strong organic acid such as trifluoromethane sulfonic acid (TFMSA), or alternatively with a weaker organic acid such as TFA in combination with a silating agent such as TMSOTf to remove all amino and hydroxyl protecting groups. (See, James P. Tam, "Acid Deprotection Reactions in Peptide Synthesis" in *Macromolecular Sequencing and Synthesis, Selected Methods and Applications*, D. H. Schlesinger, 1988, pages 153–184). The resulting unprotected peptide is desalted by adsorption chromatography on Amberlite XAD-16 resin, then coupled with compound III by means well known in the art to yield the final LHRH antagonist. In particular, this coupling may be carried out at 0°–10° C. in NMP in the presence of HOOBt, EDC.HCl, and NMM or 2,4,6-collidine, with $CuCl_2.H_2O$ added as a racemization suppressant. As an optional step, the resulting product may be desalted and the trifluoroacetate and trifluoromethanesulfonate counter ions exchanged to acetate by adsorption chromatography on Amberlite XAD-16. This material may then be purified by any means known to those of ordinary skill in the art, such as by reverse-phase chromatography on a C-18 resin using an acetonitrile/water/acetic acid mobile phase. When such reverse-phase chromatography is performed, the purified product is isolated from the chromatographic product pool by applying that pool to an weak acid ion-exchange column. The column is eluted with methanol to remove any water, then the product is eluted from the column with a methanol/acetic acid mixture. The product-containing fractions are pooled, concentrated to dryness, and the resulting oil is dissolved in glacial acetic acid and lyophilized to yield the desired LHRH antagonist as a white powder.

It is also important to note that a valuable consequence of the synthetic process is the selectivity of the acylating reaction which occurs between compounds III and IV. For example, although two reactive amino groups are available on compound IV (specifically, the serine α-amine and the isopropyllysine ε-amine), the reaction of the C-terminal amino acyl residue of compound III (i.e. D-3Pal-OH) occurs primarily on the serine α-amine, to an extent of about 90% or greater. That is, in the present invention, convergent coupling of compounds III and IV results in about 90% or greater of the desired LHRH antagonist rather than a product acylated at the isopropyllysine ε-amine. Furthermore, in the coupling of compounds I and II, a similar selectively occurs between the α and ε-nitrogens of isopropyllysine, such that about 90% or greater of the resulting product is compound IV rather than a compound acylated at the isopropyllysine ε-amine.

Intermediate compounds I, II and III may themselves be produced through a variety of pre-intermediates. "Pre-intermediate" as used herein refers to any peptide which consists of at least two amino acid residues and is used in the process of making either compound I, II or III. For ease in representing the various pre-intermediates, they have been grouped into categories designated as A, B and C. Pre-intermediates that are useful in the process of making compound I are those in Group A, those useful in the process of making compound II are in Group B and those that are useful in the process of making compound III are listed in Group C. Representative examples of useful Groups A, B and C pre-intermediates include the following:

| Group A: | | |
|---|---|---|
| 1) | $P^1$—Pro—D—AlaNH$_2$ | (A$_1$), |
| 2) | $P^1$—Lys(P$^5$)—Pro—D—AlaNH$_2$ | (A$_2$) |
| 3) | $P^1$-aa$_1$-Lys(P$^5$)—Pro—D—AlaNH$_2$ | (A$_3$) |
| Group B | | |
| 1) | $P^1$—D—Lys(Nic)—Leu—O—P$^4$ | (B$_1$), |
| 2) | H—NMeTyr(P$^3$)—D—Lys(Nic)-aa$_1$-O—P$^4$ | (B$_2$), |
| 3) | $P^1$—Ser(P$^2$)—NMeTyr(P$^3$)—D—Lys(Nic)-aa$_1$-O—P$^4$ | (B$_3$); |
| Group C | | |
| 1) | $P^1$—D—4ClPhe—D—3Pal—O—P$^4$ | (C$_1$), |
| 2) | $P^1$—D—2Nal—D—4ClPhe—D—3Pal—O—P$^4$ | (C$_2$), and |
| 3) | Q—D—2Nal—D—4ClPhe—D—3Pal—O—P$^4$ | (C$_3$). |

Unless otherwise indicated aa$_1$ is either absent or is Leu, Q is N-acetyl or THF-Gly, $P^1$ is an amino protecting group, $P^5$ is an amino protecting group orthogonal to $P^1$, $P^2$ and $P^3$ are —OH protecting groups and $P^4$ is a carboxyl protecting group, the P groups being defined below.

Synthesis of the pre-intermediate compounds is also performed by standard methods of solution phase chemistry known to those of ordinary skill in the art. Generally, these methods comprise adding a suitably protected amino acid to a growing peptide chain (referred to hereinafter as "stepwise synthesis"). The starting amino acid and any oligopeptide derivatives thereof are commercially available or, where novel in the compounds of this invention, are synthesized by methods detailed herein from readily available starting materials.

Normally, in the process of stepwise synthesis, any functional group, but in particular, either the amino or carboxyl group of the first amino acid is protected by a suitable protecting group. The next amino acid in the sequence having the complimentary (amino or carboxyl) group suitably protected, is then added to the protected or derivatized amino acid under conditions conducive to forming the amide linkage. The protecting group is then removed (or selectively removed where one or more side groups on the growing chain are also protected) from this newly added amino acid residue and the next amino acid (suitably protected) is added, and so forth.

The coupling of successive protected amino acids can be carried out in any manner well known in the art. The removal of the alpha-N-protecting groups may be performed in the presence of, for example, a solution of trifluoroacetic acid in methylene chloride, hydrogen chloride in ethyl acetate, hydrogen chloride in dioxane, hydrogen chloride in acetic acid, or other suitably strong acid solution, preferably trifluoroacetic acid in methylene chloride or hydrogen chloride in ethyl acetate. Similarly, the removal of other alpha N-, and epsilon N-protecting groups may be carried out by methods well known in the art. The deprotected peptide is then coupled with a suitably protected amino acid. Each protected amino acid is usually introduced in excess (1.01 to 2.0 equivalents) and the coupling is carried out using the appropriate reagent. In instances where the coupling is mediated by a carbodiimide, N,N'-dicyclohexylcarbodiimide, N,N'-diisopropylcarbodiimide, 1-(3-dimethylaminopropyl)-3-ethylcarbodiimide hydrochloride or some other suitable reagent, it may be mediated either alone or in the presence of 1-hydroxybenzotriazole, 3-hydroxy-1,2,3-benzotriazin-3(4H)-one, N-hydroxysuccinimide, other succinimides or oximes. Alternatively, protected amino acid active esters (e.g. p-nitrophenyl, pentafluorophenyl N-hydrosuccinimidyl and the like), symmetrical anhydrides or mixed anhydrides may be used. Additional additives like cupric chloride may also be used in the coupling reaction under special circumstances where additional racemization suppression is needed.

The use of protecting groups is well known in the art for protecting against undesirable reactions during a synthetic procedure and many such protecting groups are known (see for example, T. H. Greene and P. G. M. Wuts, *Protective Groups in Organic Synthesis*, 2nd edition, John Wiley & Son, New York, 1991, incorporated herein by reference). In the solution phase method of preparing peptides, the alpha-amino function of the amino acids is protected by an acid or base sensitive group, groups susceptible to cleavage by hydrogenation or photolysis, or by groups which may be transformed into labile protecting groups. Such protecting groups should have the properties of being stable to the conditions of peptide linkage formation, while being readily removable without destruction of the growing peptide chain or racemization of any of the chiral centers contained therein.

Examples of acid-sensitive groups are 1-adamantyloxycarbonyl (Adoc), t-butyloxycarbonyl(Boc), 1-methyl-1-(4-biphenyl)ethoxycarbonyl (Bpoc), benzyloxycarbonyl (Cbz), p-methoxybenzyloxycarbonyl (Moz), 2-nitrophenylsulfenyl (Nps), and the like. Examples of base-sensitive groups are 2,2,2 trichloroethyloxycarbonyl (Tce), 9-fluorenylmethyloxycarbonyl (Fmoc), trifluoroacetyl (Tfa), p-nitrobenzyloxycarbonyl, and the like. Examples of protecting groups which may either be transformed into labile groups or which require assisted cleavage are allyloxycarbonyl (Alloc), 2-methylthioethyloxycarbonyl, 2-methylsulfonylethyloxycarbonyl, 2-(p-toluenesulfonyl) ethyl, 1,1 -dimethyl-2-cyanoethyloxycarbonyl, and the like. The Boc, Cbz and Fmoc protecting groups are preferred.

For use in protecting side chain amino groups, a protecting moiety can be selected from any of those described above, but preferably possesses the property of orthogonality. As used in the art of peptide chemistry, an orthogonal protecting group is one which is selectively retained on a peptide during the removal of a second protecting group or selectively removed during the retention of a second protecting group. Particularly preferred protecting groups for side-chain amines are Boc, Cbz and Fmoc.

For use in protecting side chain —OH functionalities, both hydroxyl and phenolic protecting groups may be used and are referred to herein as "—OH protecting groups". Representative examples include acetyl and substituted carboxylic acid esters, methyl, methoxymethyl, phenylmethyl, t-butoxymethyl, tetrahydropyranyl, 2,2,2-trichloroethoxymethyl, p-methyoxybenzyl, o-nitrobenzyl, p-nitrobenzyl, benzyl, 2,6-dichlorobenzyl, trimethylsilyl, t-butyldimethylsilyl, t-butyldiphenylsilyl, diphenylmethylsilyl, methyloxycarbonyl, 9-fluorenylmethyloxycarbonyl, o-bromobenzyloxycarbonyl, 2,2,2-trichloroethyloxycarbonyl and the like. Particularly preferred are the benzyl, 2,6 dichlorobenzyl and the o-bromobenzyloxycarbonyl groups which also have the property of orthogonality when needed for the synthesis.

For use in protecting carboxylic acids, 9-fluorenylmethyl, methoxymethyl, benzyl and substituted benzyl, 2,2,2-trichloroethyl, methylthiomethyl, benzyloxymethyl, t-butyl, methyl, ethyl, cyclohexyl, allyl, trimethylsilyl and the like may be used. Particularly preferred are methyl, ethyl, benzyl, allyl and 9-fluorenylmethyl, chosen in such a manner to have orthogonality with the other protecting groups in the synthesis when and if desired.

It is particularly important to note that the manner of making the pre-intermediate compounds of Groups A, B and C also contributes to the overall efficiency in the process of making the desired LHRH antagonist. For example, in a particularly preferred method, compound I is prepared from a pre-intermediate $A_2$ having the formula $P^1$-aa$_1$-Lys($P^5$)-Pro-D-AlaNH$_2$ wherein aa$_1$ is as defined above and $P^5$ is an amino protecting group orthogonal to $P^1$ (see Example 3). Preparing compound I in this manner circumvents the need to incorporate a derivative of N-isopropyllysine into a growing $P^1$-Pro-D-AlaNH$_2$ chain. This is advantageous to the process since N-isopropyllysine derivatives are both difficult to handle and to obtain commercially.

In another preferred embodiment, compound II is prepared from a pre-intermediate $B_3$ having the formula $P^1$-Ser($P^2$)-NMeTyr($P^3$)-D-Lys(Nic)-aa$_1$-O-$P^4$ wherein aa$_1$ is as defined above and $P^4$ is allyl. In a particularly preferred embodiment, pre-intermediate $B_3$ is also produced by stepwise synthesis from a compound $B_2$ having the formula H-NMeTyr($P^3$)-D-Lys(Nic)-aa$_1$-O-$P^4$ which in turn was prepared from compound $B_1$ having the formula $P^1$-D-Lys(Nic)-aa$_1$-O-$P^4$ where again, the $P^4$ protecting group is allyl. Although many possible $P^4$ protecting groups may be used in the preparation of this pre-intermediate, the use of the allyl group is preferred because it may be removed under conditions which do not racemize either the α-carbon of the C-terminal residue of the peptide or the α-carbon of the N-methyltyrosine residue.

In another preferred embodiment, compound III is prepared from a compound $C_3$ wherein Q is THF-Gly. Compound $C_3$ is preferably prepared by coupling THF-Gly-OH with a compound $C_2$ having the formula $P^1$-D-2Nal-D-4ClPHe-D-3Pal-O-$P^4$. Preferably, THF-Gly-OH is prepared by reacting the dicyclohexylamine salt of tetrahydrofuroic acid (THFA.DCHA) with the p-toluenesulfonic acid salt of Gly-O-$P^4$ (TsOH-Gly-O-$P^4$), adding EDC.HCl and then hydrogenating the resulting product. Preparing compound III in this manner eliminates an additional step of first isolating the THFA moiety from the dicyclohexylamine salt prior to reacting it with TsOH-Gly-O-$P^4$. Thus, numerous methods of preparing pre-intermediate compounds I, II and III by solution and/or solid phase peptide chemistry are intended to fall within the scope of the invention and preferably, such methods eliminate the need for multiple purification steps during the total synthetic process.

Representative reactions schemes for preparing the pre-intermediates of Groups A, B and C are presented below. The reactions schemes shown are only meant to represent the manner of making the preferred pre-intermediates and are not intended to limit the scope of the invention.

Scheme II: Synthetic Scheme IIa depicts the process for making pre-intermediate compounds of Group A, designated $A_1$, and $A_2$, leading to the synthesis of compound Ia and pre-intermediate compounds of Group B, designated $B_{1a}$, $B_{2a}$, and $B_{3a}$, leading to the synthesis of intermediate compound IIa. Synthetic Scheme IIb depicts an alternative process whereby the pre-intermediate compounds of Group A are also used in preparing a compound Ib. Also shown in Scheme IIb is an alternative process for making pre-intermediate compounds of Group B, designated $B_{2b}$, and $B_{3b}$, leading to the synthesis of intermediate compound IIb. Scheme IIc depicts a process for making another pre-intermediate Group A compound, designated $A_3$, also leading to the synthesis of compound Ib.

SCHEME IIa

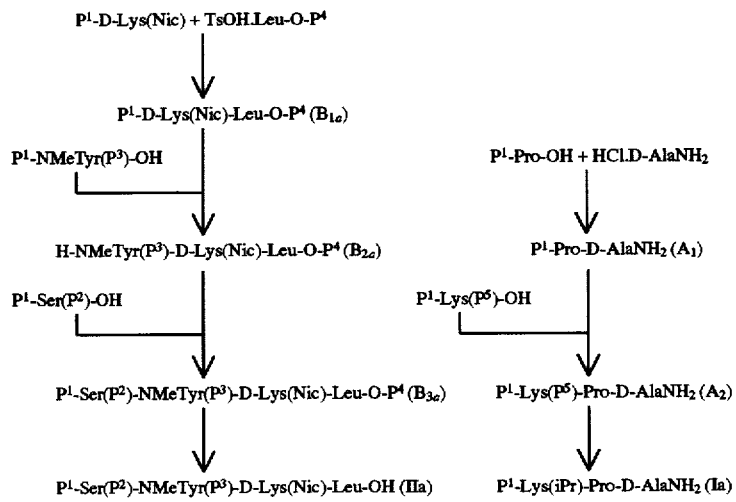

SCHEME IIb

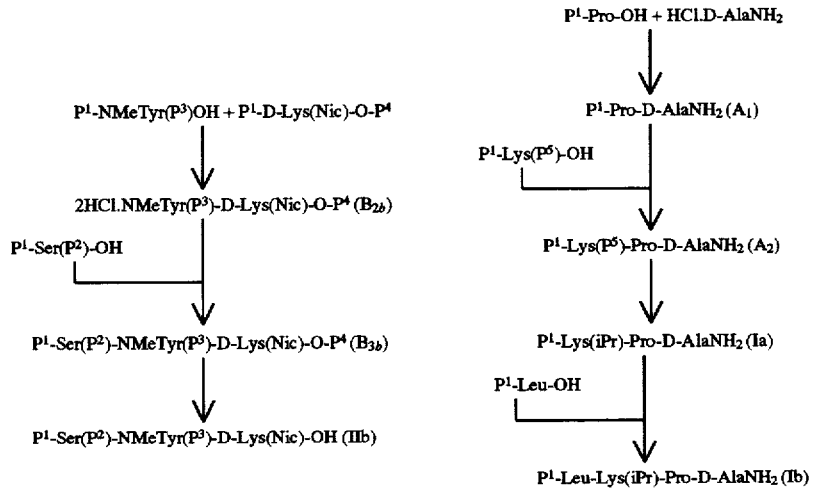

SCHEME IIc

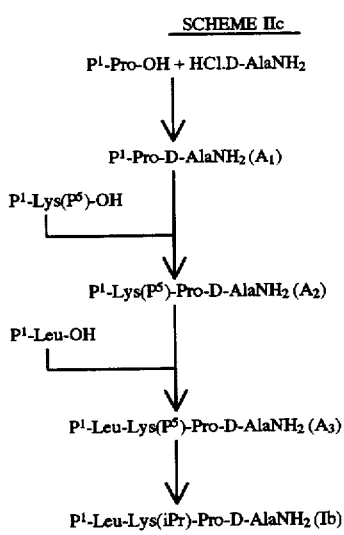

Scheme III: Synthetic Scheme III depicts a synthetic process for making pre-intermediate compounds of Group C, designated $C_1$, $C_2$, and $C_3$, leading to the synthesis of compound III.

SCHEME III

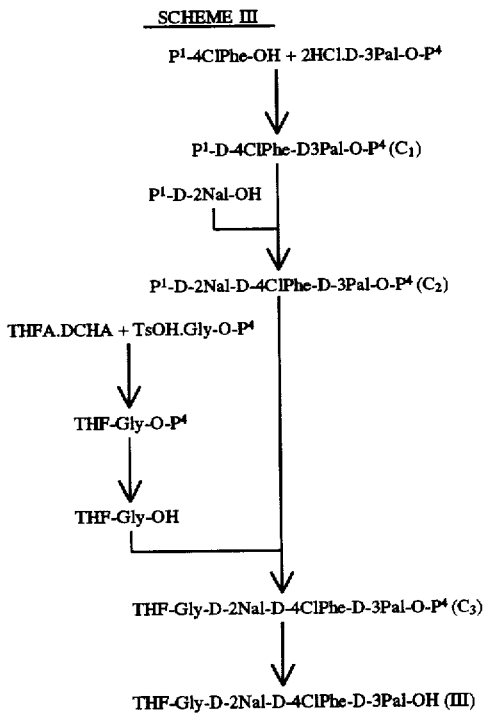

Representative pre-intermediate compounds of the present invention include the compounds identified as follows:

(a) Boc-Ser(Bzl)-NMeTyr(Bzl)-D-Lys(Nic)-Leu-O-All;
(b) Boc-Ser(Bzl)-NMeTyr(Bzl)-D-Lys(Nic)-Leu-O-Bzl;
(c) Boc-Ser(Bzl)-NMeTyr(Bzl)-D-Lys(Nic)-Leu-O-Me;
(d) Boc-Ser(Bzl)-NMeTyr(Bzl)-D-Lys(Nic)-O-All;
(e) Boc-Ser(Bzl)-NMeTyr(Bzl)-D-Lys(Nic)-O-Bzl;
(f) Boc-Ser(Bzl)-NMeTyr(Bzl)-D-Lys(Nic)-O-Me;
(g) Boc-Ser(Bzl)-NMeTyr($Cl_2$Bzl)-D-Lys(Nic)-Leu-O-All;
(h) Boc-Ser(Bzl)-NMeTyr($Cl_2$Bzl)-D-Lys(Nic)-Leu-O-Bzl;
(i) Boc-Ser(Bzl)-NMeTyr($Cl_2$Bzl)-D-Lys(Nic)-Leu-O-Me;
(j) Boc-Ser(Bzl)-NMeTyr($Cl_2$Bzl)-D-Lys(Nic)-O-All;
(k) Boc-Ser(Bzl)-NMeTyr($Cl_2$Bzl)-D-Lys(Nic)-O-Bzl;
(l) Boc-Ser(Bzl)-NMeTyr($Cl_2$Bzl)-D-Lys(Nic)-O-Me;
(m) H-NMeTyr(Bzl)-D-Lys(Nic)-Leu-O-All;
(n) H-NMeTyr(Bzl)-D-Lys(Nic)-Leu-O-Bzl;
(o) H-NMeTyr(Bzl)-D-Lys(Nic)-Leu-O-Me;
(p) H-NMeTyr(2$Cl_2$Bzl)-D-Lys(Nic)-Leu-O-All;
(q) H-NMeTyr(2$Cl_2$Bzl)-D-Lys(Nic)-Leu-O-Bzl;
(r) H-NMeTyr(2$Cl_2$Bzl)-D-Lys(Nic)-Leu-O-Me;
(s) Boc-D-Lys(Nic)-Leu-O-All;
(t) Boc-D-Lys(Nic)-Leu-O-Bzl;
(u) Boc-D-Lys(Nic)-Leu-O-Me;
(v) Boc-D-2Nal-D-4ClPhe-D-3Pal-O-All;
(w) Boc-D-2Nal-D-4ClPhe-D-3Pal-O-Bzl;
(x) Boc-D-2Nal-D-4ClPhe-D-3Pal-O-Me;
(y) THF-Gly-D-2Nal-D-4ClPhe-D-3Pal-O-All;
(z) THF-Gly-D-2Nal-D-4ClPhe-D-3Pal-O-Bzl;
(aa) THF-Gly-D-2Nal-D-4ClPhe-D-3Pal-O-Me;
(bb) THF-Gly-O-All;
(cc) THF-Gly-O-Bzl;
(dd) THF-Gly-O-Me;
(ee) Cbz-Pro-D-AlaNH$_2$; and
(ff) Boc-Lys(Cbz)-Pro-D-AlaNH$_2$ The compounds and processes of the present invention may be better understood by reference to the following examples which are provided for illustration and are not intended to limit the scope of the inventive concept. Unless otherwise specified, all reagents were purchased from commercial suppliers such as Aldrich Chemical (Milwaukee, Wis.) and Synthetech, Inc. (Albany, Oreg.).

EXAMPLE 1

Cbz-Pro-D-Ala-NH$_2$

A solution of Cbz-Pro-OH (10.1 gm) in 2-propanol (IPA, 100 mL) was cooled to −5° C., and NMM (4.4 mL) was added with additional cooling to −10° C. iso-Butyl chloroformate (5.2 mL) was added dropwise while maintaining the temperature at −10° to −15° C. After the addition was complete, a solution of HCl.D-Ala-NH$_2$ (5.0 gm) and NMM (4.4 mL) in water (50 mL) was added and the mixture was stirred at −10° C. for another 30 minutes. The cooling bath was then removed and the solution stirred another three hours. The reaction was quenched in a mixture of EtOAc (200 mL) and water (100 mL) containing NaHCO$_3$ (5 gm) and NaCl (5 gm). The layers were separated and the aqueous layer extracted with EtOAc (2×100 mL). The organic layers were combined and washed with water (2×50 mL) and then concentrated in vacuo to dryness. The residue was taken up in EtOAc (250 mL) and the solution washed with water (2×50 mL) to remove any residual IPA. The organic solution was concentrated in vacuo to about 50 mL and treated with EtOAc (50 mL) and heptane (50 mL) and the product crystallized. The solids were filtered, washed on the filter with heptane and dried in vacuo to yield 8.2 gm Cbz-Pro-D-Ala-NH2. HPLC: 99.2 pa %, $[\alpha]_D$=−11.2 (CHCl$_3$).

EXAMPLE 2

Boc-Lys(Cbz)-Pro-D-Ala-NH$_2$

A. Deprotection

A solution of Cbz-Pro-D-Ala-NH$_2$ (9.3 gm) and p-toluenesulfonic acid (6.09 gm) in isopropanol (IPA, 60 mL) and water (10 mL) was hydrogenated over 5% Pd/C at 40 psig and ambient temperature. The catalyst was filtered off, washed with 10% water-IPA (20 mL) and the combined filtrates were evaporated to dryness in vacuo. Acetonitrile (ACN, 126 mL) was added to the residue and the mixture again evaporated to about 100 mL in vacuo, and this process repeated four times.

B. Coupling

To the suspension from above were added Boc-Lys(Cbz)-OH (12.17 gm), HOBt (5.35 gm) along with ACN (100 mL). The suspension was cooled to 0°–5° C. and NMM (8.5 mL) was added followed by a suspension of EDC (7.34 gm) in ACN (57 mL). The mixture was stirred at 0°–5° C. for one hour and at room temperature overnight. The mixture was then evaporated to dryness in vacuo, and the residue partitioned between EtOAc (420 mL), water (60 mL) and 10% Na$_2$CO$_3$ (100 mL). The layers were separated and the aqueous layer was extracted with EtOAc (2×200 mL). The organic extracts were combined and washed with 10% citric acid (2×50 mL), 10% Na$_2$CO$_3$ (2×53 mL) and water (40 mL and evaporated in vacuo to about 115 mL. EtOAc (135 mL) was added and the solution again evaporate in vacuo to about 115 mL and this process was then repeated. Heptane (135 mL) was added to the EtOAc solution over about two hours and the product crystallized. The solids were filtered, washed with heptane and dried in vacuo to yield 14.8 gm of Boc-Lys(Cbz)-Pro-D-Ala-NH$_2$ HPLC: 99.2%, MS: (M+H)$^+$=548, (M+NH$_4$)$^+$=565

EXAMPLE 3

Boc-Lys(iPr)-Pro-D-Ala-NH$_2$

A solution of Boc-Lys(Cbz)-Pro-D-Ala-NH$_2$ (80 gm) in 2-propanol (IPA, 800 mL) and acetone (108 mL) was hydrogenated over 4% Pd/C at 60 psi hydrogen. The catalyst was filtered off and rinsed with EtOAc, and the filtrate evaporated in vacuo to dryness. The residue was taken up in EtOAc (700 mL) and again evaporated in vacuo to dryness, and this procedure was repeated once. After dissolving the residue in EtOAc (250 mL) the solution was triturated with heptane (200 mL). The mixture was evaporated in vacuo to yield a solid which formed a suspension when treated with EtOAc (250 mL). The suspension was treated with heptane (100 mL), filtered and dried in vacuo to yield 64.2 gm Boc-Lys(iPr)-Pro-D-Ala-NH$_2$. HPLC: 98.5 pa %, MS: (M+H)$^+$=456

EXAMPLE 4

Boc-Lys(iPr,Fmoc)-Pro-D-Ala-NH$_2$

A solution of Boc-Lys(iPr)-Pro-D-Ala-NH$_2$ (9.11 gm) in 10% Na$_2$CO$_3$ (25 mL) and THF (30 mL) was cooled to 0° C. and treated with a solution of Fmoc-Cl (6.46 gm) in THF. After 1 hour at 0° C. the mixture was partitioned between EtOAc (200 mL) and water (100 mL) and the layers were separated. The organic layer was washed with water (100 mL), 10% citric acid (2×100 mL) and water (100 mL), then dried over Na$_2$SO$_4$ and evaporated to dryness to yield an oil. The residue was dissolved in EtOAc and precipitated from heptane to yield 11.66 gm of crude product. This material was dissolved in a small in EtOAc and loaded onto a silica gel (200 gm) column which was eluted with an EtOAc/heptane mixture (2/1), followed by EtOAc and finally by ethanol. The product-containing fractions were combined and evaporated in vacuo to dryness to yield an oil. The residue was dissolved in a small amount of EtOAc and precipitated from heptane to yield 10.75 gm of Boc-Lys(iPr, Fmoc)-Pro-D-Ala-NH$_2$. HPLC: 98.1%, MS: (M+H)$^+$=678, (M+NH$_4$)$^+$=695, [a]D=−12.2 (c=1, HOAc)

EXAMPLE 5

Boc-Leu-Lys(iPr,Fmoc)-Pro-D-Ala-NH$_2$

A. Deprotection

A solution of Boc-Lys(iPr,Fmoc)-Pro-D-Ala-NH$_2$ (15.0 gm) in EtOAc (200 mL) was cooled in an ice bath while HCl gas was bubbled through the solution until it was saturated, then stirred for an additional 20 minutes at 0° C. The solution was sparged with nitrogen overnight to remove HCl, then heptane was added to precipitate the deprotected peptide. The solids were filtered and dried in vacuo to yield 12.3 gm of HCl.Lys(iPr,Fmoc)-Pro-D-Ala-NH$_2$.

B. Coupling

The deprotected peptide (section A, 11.1 gm) was dissolved in NMP (30 mL) and neutralized with NMM (2.1 mL). Boc-Leu-OH (4.69 gm) and HOBt (3.33 gm) were then added, and the mixture was cooled to 5° C. and EDC.HCl (3.82 gm) added. The pH was adjusted to 7 with NMM (2.1 mL) in order to drive the reaction to completion. After two hours the reaction was partitioned between EtOAc (400 mL) and 5% citric acid (200 mL). The layers were separated and the aqueous layer extracted with EtOAc (200 mL) The organic layers were combined and washed with 5% citric acid (200 mL), 5% NaHCO$_3$ (2×200 mL) and water (20C mL) and dried over MgSO$_4$. The EtOAc was evaporate in vacuo to yield an oil. This material was taken up in a sma!! mount of EtOAc and applied to a silica gel (400 gm) colum. which was eluted with an EtOAc/heptane mixture. Th product-containing fractions were combined and evaporat in vacuo to dryness to yield 9.91 gm of Boc-Leu-Lys(iPr Fmoc)-Pro-D-Ala-NH$_2$. HPLC: 97.9 pa %, [α]$_D$=−2: o (c=1, HOAc), (M+H)$^+$=791

EXAMPLE 6

Boc-D-Lys(Nic)-Leu-Lys(iPr,Fmoc)-Pro-D-Ala-NH

A. Deprotection

A solution of Boc-Leu-Lys(iPr,Fmoc)-Pro-D-Ala-NH$_2$ (5.59 gm) was treated with an HCl/EtOAc solution (15( nL) at 0±5° C. for 60 min. Heptane (30 mL) was added an.1 the solution was sparged with nitrogen for 30 min. the was concentrated in vacuo to about one-half of the o: ginal volume. An EtOAc/heptane mixture (40 mL/40 ml was added and the solution again concentrated in vacuo one half volume. Another portion of an EtOAc/heptane xture (40 mL/40 mL) was added and the mixture concent ted in vacuo to dryness. Ethyl acetate (50 mL) and the r sulting precipitate was filtered and dried in vacuo to yield 43 gm of HCl.D-Leu-Lys(iPr,Fmoc)-Pro-D-Ala-NH$_2$.

B. Coupling

The deprotected tetrapeptide from above (sectio A, 4.20 gm) was dissolved in NMP (35 mL) along with H Bt (0.98 gm), Boc-D-Lys(Nic)OH (2.13 gm) and NMM ( 27 mL). The solution was cooled to 5±5° C., and EDC.HCl 1.16 gm) was added. After one hour the ice bath was remo 1 and the mixture stirred another hour at ambient tempe ure. The reaction mixture was partitioned between EtOAc (100 mL) and water (50 mL). The layers were separated and the aqueous layer extracted with EtOAc (100 mL). The combined organic extracts were washed with 5% citric acid (2×50 mL), 5% NaHCO$_3$ (2×50 mL) and water (2×50 mL), then concentrated in vacuo to yield 6.15 gm of an oil. The oil was dissolved in EtOAc (25 mL) and added to ether (500 mL) and a precipitate formed. The solids were filtered and dried in vacuo to yield 5.13 gm Boc-D-Lys(Nic)-Leu-Lys(iPr,Fmoc)-Pro-D-Ala-NH$_2$.

EXAMPLE 7

Boc-NMeTyr(Bzl)-D-Lys(Nic)-Leu-Lys(iPr,Fmoc)-Pro-D-Ala-NH$_2$

A. Deprotection

A solution of Boc-D-Lys(Nic)-Leu-Lys(iPr,Fmoc)-Pro-D-Ala-NH$_2$ (6.75 gm) in EtOAc (20 mL) was treated with an Hcl/EtOAc solution (150 mL) at 5±5° C. for one hour then at ambient temperature for 30 minutes. Heptanes (30 mL) were added and the mixture sparged with nitrogen for 10 minute. The solids were filtered and dried in vacuo at 40° C.

B. Coupling

A solution of the deprotected peptide from above (Section A), Boc-NMeTyr(Bzl)-)H, and HOBt in NMP was cooled to 5±5° C., then the solution was treated with NMM (3.2 mL) until the pH was about 5. EDC (1.33 gm) was added and the mixture was stirred overnight at ambient temperature. The reaction mixture was partitioned between EtOAc (200 mL) and H$_2$O (100 mL) and the layers were separated. The aqueous layer was extracted with EtOAc (200 mL) and the organic layers were combined and washed with 5% citric acid (2×100 mL), 10% K$_2$CO$_3$ (2×100 mL) and water (100 mL), and concentrated to dryness in vacuo. The resulting oil was dissolved in EtOAc (15 mL) and the solution was applied to a silica gel (300 gm) column. The column was eluted successively with 5% EtOH/EtOAc, 10% EtOH/EtOAc and 15% EtOH/EtOAc. The product-containing fractions were combined and concentrated to dryness in vacuo. The residue was taken up in a small amount of EtOAc and precipitated from a mixture of heptane (150 mL) and MTBE (1 mL) to yield 4.54 gm of Boc-NMeTyr(Bzl)-D-Lys(Nic)-Leu-Lys(iPr,Fmoc)-Pro-D-Ala-NH$_2$. MS: (M+H)$^{30}$=1291, (M-K)=1329.

EXAMPLE 8

Boc-D-Lys(Nic)-Leu-O-Bzl

The tosylate salt of Leu-O-Bzl (61.6 gm) was partitioned between EtOAc (200 mL) and 10% K$_2$CO$_3$ (400 mL). The layers were separated and the aqueous layer extracted with EtOAc (200 mL). The organic layers were combined and washed with water (2×50 mL) and concentrated in vacuo to about 200 mL. Ethyl acetate (250 mL) was added and the solution again concentrated in vacuo to about 200 mL, and this procedure repeated with a final concentration in vacuo to about 100 mL. A small amount of NMM (1.6 mL) was added to the solution and it was held for further processing.

In a separate flask, Boc-D-Lys(Nic)-OH (50.0 gm) was dissolved in THF and the solution cooled to 0° C. N-Methyl morpholine (15.7 mL) was added, then the solution was cooled to -10° to -5° C. and iso-butyl chloroformate (19.1 mL) was added dropwise maintaining the temperature below -5° C. After the addition was complete, the solution was stirred another 20 minutes at -5° C., then the Leu-O-Bzl solution from above was added while maintaining the temperature at -5° C. The mixture was stirred overnight while attaining ambient temperature, then partitioned between EtOAc (3 L) and 10% citric acid (500 mL). The layers were separated and the organic layer washed with 10% citric acid (500 mL), 10% NaHCO$_3$ (2×500 mL) and water (500 mL). The organic layer was concentrated in vacuo to about 1 L, then treated with EtOAc (2 L) and concentrated in vacuo to about 750 mL. The residue was again treated with EtOAc (2 L) and evaporated in vacuo to about 750 mL, then treated with heptane (1 L). After stirring overnight, the precipitate was filtered, washed on the filter with heptane and dried in vacuo to yield 66.6 gm Boc-D-Lys(Nic)-Leu-O-Bzl. HPLC: 98.7 pa %, [α]$_D$=14.1 (c=0.92, CHCl$_3$), (M+H)$^+$=555

EXAMPLE 9

NMeTyr(Bzl)-D-Lys(Nic)-Leu-O-Bzl

A. Deprotection #1

A solution of Boc-D-Lys(Nic)-Leu-O-Bzl (60 gm) in 2.3N HCl/EtOAc (2.5 L) was stirred at ambient temperature for 2 hours, then HCl gas was bubbled through the solution for 10 minutes. After stirring an additional 30 minutes, the solvent was evaporated in vacuo to dryness. The residue held in vacuo overnight, then dissolved in DMF (225 mL) and held for further processing. (Section B)

B. Coupling

A solution of Boc-NMeTyr(Bzl)-OH (40.6 gm) in THF (480 mL) was cooled to -3° to -10° C. and NMM (13.2 mL) was added followed by iso-butyl chloroformate (ICBF, 14.9 mL). The mixture was stirred for 30 minutes after the addition of ICBF was complete, then the solution from above (Section A) was added dropwise maintaining the temperature below -5° C. This was immediately followed by the addition of NMM (26.4 mL) and the mixture was stirred overnight while attaining ambient temperature. The reaction mixture was added to EtOAc (1.7 L) and the resulting solution washed with pH 2.5 H3PO$_4$ (3×300 mL), 5% NaHCO$_3$ (3×300 mL) and water (3×300 mL). The EtOAc was evaporated to yield an oil.

C. Deprotection #2

The oil from above (Section B) was dissolved in EtOAc (600 mL), and this solution was added slowly to a mixture of 3.0N HCl/EtOAc (3.8 L) and EtOAc (200 mL). After stirring three hours, MTBE (2.5 L) was added and the resulting precipitate filtered, washed on the filter with MTBE and dried in vacuo to yield 74.1 gm 2HCl.NMeTyr(Bzl)-D-Lys(Nic)-Leu-O-Bzl.

D. Neutralization

The tripeptide dihydrochloride (50.2 gm) was partitioned between EtOAc (500 mL) and 10% K$_2$CO$_3$ (100 mL) and water (100 mL). An emulsion formed and methylene chloride (DCM, 150 mL) was added and the emulsion broke partially. The layers were separated and the aqueous layer extracted with EtOAc (250 mL). The organic layers were combined and washed twice with water and evaporated in vacuo to dryness. The residue was treated with EtOAc (350 mL) and DCM (150 mL) and concentrated in vacuo to dryness and this procedure repeated twice to yield a solid in the flask. The solid was treated with EtOAc (200 mL) and heptane (400 mL), filtered, washed on the filter with heptanes and dried in vacuo to yield 40.6 gm NMeTyr(Bzl)-D-Lys(Nic)-Leu-O-Bzl. HPLC: 96.9 pa %, [α]$_D$=25.9 (c=1, HOAc)

EXAMPLE 10

Boc-D-Lys(Nic)-Leu-O-All

A mixture of Boc-D-Lys(Nic)OH (30.0 gm), HOBt (15.7 gm), TsOH.Leu-O-All (31.3 gm) and NMP (225 mL) was cooled to 0°±5° C. and a solution of EDC.HCl (17.8 gm) in water (18 mL) was added, followed by NMM (20 mL) and the solution stirred at 0°±5° C. for one hour followed by stirring at ambient temperature overnight. The reaction mixture was partitioned between EtOAc (1 L) and water (500 mL), and the layers separated. The organic layer washed with 10% citric acid (2×210 mL), 10% $K_2CO_3$ (210 mL) and water (2×210 mL). The organic solution was evaporated to dryness in vacuo and the resulting oil was taken up in EtOAc (100 mL) and stirred with heptane (160 mL) until cloudy. The mixture was seeded, stirred for 4 hours, then treated with an additional portion of heptane (110 mL). After stirring 2 hours at 10°±5° C., the solids were filtered, rinsed on the filter with EtOAc/heptane (1/3, 80 mL) and dried in vacuo to yield 35.3 gm Boc-D-Lys(Nic)-Leu-O-All. HPLC: 94.1 pa %, $[\alpha]_D$=15.1 $(CHCl_3)$,$(M+H)^+$=505

EXAMPLE 11

NMeTyr(Bzl)-D-Lys(Nic)-Leu-O-All

A. Deprotection #1

A solution of Boc-D-Lys(Nic)-Leu-O-All (20 gm) in 3.9N HCl/EtOAc (120 mL) was stirred 40 minutes, and the solution was then evaporated in vacuo to about 20 mL. The residue was treated with EtOAc (150 mL) and again evaporated in vacuo to about 30 mL and the residue diluted with NMP (80 mL) and evaporation in vacuo continued until distillation ceased. The resulting solution was held for further processing. (Section B)

B. Coupling

A solution of Boc-NMeTyr(Bzl)OH (16.8 gm) and HOBt (7.28 gm) and the solution from above (Section A) was cooled to 0°±5° C. and a slurry of EDC.HCl (11.9 gm) in EtOAc (50 mL) was added followed by NMM (13.2 mL). The mixture was stirred at 0°±5° C. for 30 minutes, then 2 hours at ambient temperature. The reaction mixture was partitioned between EtOAc (800 mL) and 10% citric acid (240 mL). The aqueous layer was extracted with EtOAc and the organic extracts combined and washed with 10% citric acid (240 mL), $K_2CO_3$ (2×240 mL) and water (200 mL). The solution was evaporated in vacuo to about 200 mL, then EtOAc (300 mL) was added and the resulting solution evaporated in vacuo to dryness to yield a solid.

C. Deprotection #2

The solid from above (section B) was dissolved in DCM (88 mL) and TFA (88 mL) and stirred at ambient temperature for 45 minutes. The mixture was partitioned between EtOAc (900 mL) and 15% $K2CO_3$ (900 mL) and the layers separated. The aqueous layer was extracted with EtOAc (450 mL) and the combined EtOAc layers were washed with water (2×240 mL) and evaporated in vacuo to about 600 mL. Another portion of EtOAc (300 mL) was added and the solution again concentrated in vacuo to about 300 mL. The solution was seeded and allowed to stir overnight at ambient temperature. Heptane (670 mL) was added and the mixture stirred an additional 5 hours at ambient temperature. The resulting solids were filtered off and washed on the filter with an EtOAc/Heptane (1/3, 200 mL) mixture and dried in vacuo at 45° C. to yield 25.3 gm of NMeTyr(Bzl)-D-Lys(Nic)-Leu-O-All. HPLC: 96.9 pa %, $[\alpha]_D$=26.7 (c=1, HOAc), $(M+H)^+$=672

EXAMPLE 12

NMeTyr(Cl$_2$Bzl)-D-Lys(Nic)-O-All

A. Deception #1

A solution of Boc-D-Lys(Nic)-Leu-O-All (20.2 gm) in EtOAc (220 mL) was treated with 2.5N HCl/EtOAc (220 mL) for 30 minutes. The solution was concentrated in vacuo to about 40 mL, then EtOAc (200 mL) was added and the solution again concentrated in vacuo to about 40 mL. The residue was treated with another portion of EtOAc (200 mL) and evaporated in vacuo to dryness, then the residue was dissolved in NMP (80 mL) and evaporated in vacuo until distillation ceased.

B. Coupling

Boc-NMeTyr(Cl$_2$Bzl)-OH (20.0 gm), HOBt (7.35 gm) and NMP 20 mL) were added to the residue from above and the mixture was cooled to 0°–5° C. In a separate flask, a suspension EDC.HCl (9.21 gm) in NMP (80 mL) was cooled to 0°–5° C. then added to the solution prepared above, followed by NMM (14.5 mL). The mixture was stirred at 0°–5° C. for 30 minutes, then at ambient temperature overnight. The reaction mixture was partitioned between EtOAc (800 mL) and 10% citric acid (180 mL), the layers were separated, and the aqueous layer was extracted with EtOAc (800 mL). the organic extracts were combined and washed with 10% citric acid (180 mL), 10% $K_2CO_3$ (2×180 mL) and water (2×180 mL), then concentrated in vacuo to about 200 mL. The concentrated was treated with EtOAc (300 mL) and the solution evaporated in vacuo to dryness.

C. Deception #2

The residue from Section B was dissolved in methylene chloride (DCM, 88 mL) and treated with TFA (88 mL) for 45 minutes. The reaction mixture was partitioned between EtOAc (900 mL) and 17% $K_2CO_3$ (900 mL), the layers separated, and the aqueous layer was extracted with EtOAc (460 mL). The organic layers were combined and washed with water (2×180 mL) and a small amount of solid at the interface was filtered off. The organic layer was concentrated in vacuo to about 600 mL. EtOAc (300 mL) was added and the solution concentrated in vacuo to about 320 mL. Seed crystals were added, the mixture stirred at ambient temperature overnight, then heptane (640 mL) was added and the slurry stirred at ambient temperature another 3 hours. The solids were filtered, washed on the filter with a mixture of EtOAc (50 mL) and heptane (150 mL), and dried in vacuo to yield 38.46 gm of NMeTyr(Cl$_2$Bzl)-D-Lys(Nic)-O-All. MS: $(M+H)^{30}$=740

EXAMPLE 13

Boc-Ser(Bzl)-NMeTyr(Bzl)-D-Lys(Nic)-Leu-OH

A. Coupling

A solution of Boc-Ser(Bzl)OH (6.0 gm) in DCM (25 mL) was cooled to 5° C. A solution of dicyclohexylcarbodiimide (2.1 gm) in DCM (5 mL) was added, then the reaction was stirred 75 minutes at 5° C., then the entire mixture was added to solid NMeTyr(Bzl)-D-Lys(Nic)-Leu-O-Bzl (6.0 gm) at ambient temperature, followed by the addition of a DCM (5 mL) rinse of the reaction flask. The reaction was then stirred overnight at ambient temperature. The precipitated dicyclohexylurea was filtered off and washed on the filter with DCM (75 mL). The combined filtrates were washed with 5% citric acid (2×20 mL), 5% NaHCO$_3$ (2×10 mL) and water (2×10 mL), then evaporated in vacuo to dryness to yield an oil. The oil was applied to a silica gel (280 gm) column and eluted with an EtOAc/MeOH (9/1) mixture. The product-containing fractions were combined and evaporated in vacuo to dryness to yield 7.9 gm of Boc-Ser(Bzl)-NMeTyr(Bzl)-D-Lys(Nic)-Leu-O-Bzl. MS: $(M+H)^+=999$ B. Deception A solution of Boc-Ser(Bzl)-NMeTyr(Bzl)-D-Lys(Nic)-Leu-O-Bzl (3.7 gm) in NMP (10 mL) was cooled to 1° C. and a solution of 2N NaOH (in water, 12.5 mL) was added dropwise over about 15 minutes, keeping the reaction temperature below 6° C. The reaction mixture was diluted with water (100 mL) and the resulting solution washed with EtOAc (3×15 mL). The aqueous layer was covered with EtOAc (25 mL) and the pH of the mixture adjusted to 2 with 6N HCl. The layers were separated and the aqueous layer extracted with EtOAc (2×20 mL). The EtOAc extracts were combined and washed with water (2×10 mL) and concentrated in vacuo to an oil. The oil was dissolved in EtOAc (8 mL) and the resulting solution added to heptane (500 mL) and the resulting slurry stirred overnight. The solids were filtered and dried in vacuo to yield 3.0 gm Boc-Ser(Bzl)-NMeTyr(Bzl)-D-Lys(Nic)-Leu-OH.

EXAMPLE 13A

Boc-Ser(Bzl)-NMeTyr(Bzl)-D-Lys(Nic)-Leu-OH

A. Coupling

A solution of Boc-Ser(Bzl) (7.95 gm) and DCM (20 mL) was cooled to 0° C. and a solution of DCC (2.76 gm) in DCM (10 mL) was added. The solution was stirred at 0°±10° C. for one hour, then filtered to remove the precipitated DCU. A slurry of NMeTyr(Bzl)-D-Lys(Nic)-Leu-O-All (6.0 gm) in DCM (25 mL) was added to the filtrate, and the solution warmed to 20°±5° C. and stirred overnight. A small amount of precipitated DCU was filtered off and the filter cake washed with DCM (50 mL) and EtOAc (45 mL). The combined filtrates were evaporated to dryness in vacuo and the residue was dissolved in EtOAc (250 mL) and heptane (25 mL). The organic solution was washed with 10% citric acid (2×40 mL), 10% $K_2CO_3$ (2×40 mL) and water (2×40 mL). The organic solution evaporated to dryness in vacuo, then dissolved in a small amount of EtOAc and applied to a silica gel (180 gm) chromatography column. The column was eluted with EtOAc/Heptane (500 mL/150 mL), then with EtOAc/heptane (125 mL/40 mL) and finally with EtOAc (4 L). The product-containing fractions were combined and evaporated to dryness in vacuo to yield Boc-Ser(Bzl)-NMeTyr(Bzl)-D-Lys(Nic)-Leu-O-All as an oil.

B. Deprotection

A solution of Pd(PPh$_3$)$_2$Cl$_2$(0.062gm) in THF (25 mL) was purged with nitrogen, then Bu$_3$SnH (0.130 gm) was added and the mixture stirred 10 minutes under nitrogen. A solution of the tetrapeptide from above in THF (33 ML) was added followed by morpholine (7.0 mL) and the mixture stirred 30 minutes, at which time the reaction was complete. The mixture was diluted with THF (30 mL), then evaporated to dryness in vacuo. The residue was taken up in EtOAc (210 mL) and water (20 mL), and the pH of the mixture was adjusted to about 3 with 2NHCl. The layers were separated and the organic layer washed with water (50 mL). The organic layer was evaporated to dryness in vacuo to about 40 mL, then added to heptane (1 L) and a precipitate formed. The solids were filtered and washed with heptane to yield 7.0 gm Boc-Ser(Bzl)-NMeTyr(Bzl)-D-Lys(Nic)-Leu-OH. MS: $(M+K)^+=947$, $(M+2K-H)^+=985$

EXAMPLE 14

Boc-Ser(Bzl)-NMeTyr(Cl$_2$Bzl)-D-Lys(Nic)-Leu-OH

A. Coupling

A solution of Boc-Ser(Bzl)-OH (12.0 gm) in DCM (23 mL) was cooled to 0°–5° C. and treated with a cold solution of dicyclohexylcarbodiimide (4.18 gm) in DCM (150 mL). After stirring one hour at 0°–5° C., a mixture of NMeTyr (Cl$_2$Bzl)-D-Lys(Nic)-Leu-OH (10.0 gm) and NMP (6 mL) in DCM (23 mL) was added while maintaining the temperature below 10° C. The mixture was stirred 30 minutes at 0°–5° C., then for 3 hours at ambient temperature. The precipitated dicyclohexylurea (DCU) was filtered off and washed with DCM (60 mL) and EtOAc (60 mL). The filtrates were combined and evaporated in vacuo to dryness. The residue was dissolved in EtOAc (450 mL) and heptane (45 mL) and cooled to 0°–10° C. and filtered to remove additional DCU. The filtrate was washed with 10% citric acid (2×60 mL), 10% K$_2$CO$_3$ (2×60 mL) and water (2×60 mL), then was evaporated in vacuo to dryness to yield an oil.

B. Purification of the Allyl Ester

The residue was dissolved in EtOAc (30 mL) and applied to a silica gel (275 gm) column. The column was eluted with an EtOAc:heptane mixture (1050 mL:450 mL) followed by EtOAc (8 L). The product-containing fractions were combined and concentrated in vacuo to dryness to yield an oil.

C. Deprotection of the Allyl Ester

The oil from above (Section C) was dissolved in THF (35 mL) under a nitrogen blanket. In a separate flask purged with nitrogen was charged (PPh3)$_2$PdCl$_2$ (0.095 gm) and THF (35 mL). Tri-n-butyltin hydride (0.182 mL) was added to the solution (color changed from yellow to red), followed by morpholine (10.6 mL), then the solution of allyl ester was added. After stirring 2 hours at ambient temperature, the mixture was concentrated in vacuo to dryness and the residue was dissolved in EtOAc (315 mL). Water (30 mL) was added to the solution, and the pH of the aqueous layer was adjusted to 1–2 with 2N HCl at temperature of 5°–15° C. After warming to ambient temperature the layers were separated and the organic layer was washed with water (90 mL). The organic solution was evaporated in vacuo to dryness, and the residue was re-dissolved in EtOAc (150 mL) and again evaporated in vacuo to dryness. The resulting oil was taken up in EtOAc (80 mL) and the product precipitated when this solution was added to heptane (1750 mL). The solids were filtered, washed on the filter with heptane (2×100 mL) and dried in vacuo to yield 12.2 gm of Boc-Ser(Bzl)-NMeTyr(Cl$_2$Bzl)-D-Lys(Nic)-Leu-OH. MS: $(M+H)^+=977$

EXAMPLE 15

Boc-NMeTyr(Bzl)-D-Lys(Nic)-O-Me

A solution of 2HCl.D-Lys(Nic)-O-Me (8.4 gm) in DMF (40 mL) was cooled in an ice bath and treated with NMM (2.75 mL) followed by HOBt (5.05 gm) and Boc-NMeTyr (Bzl)-OH (9.4 gm). The mixture was cooled to 0° to 5° C. and EDC.HCl (5.25 gm) was added followed by DMF (10 mL) and THF (25 mL). The reaction was stirred at 0° to 5° C. for one hour then at ambient temperature overnight. The pH was adjusted to 6 with NMM (2.75 mL) and the mixture was stirred another three hours at room temperature. The mixture was concentrated in vacuo, and the residue was taken up in EtOAc (11210 mL) and washed with water (100 mL), 5% NaHCO$_3$ (2×75 mL), and with water to neutral pH. The solvent was evaporated in vacuo to yield an oil which was applied to a silica gel (200 gm) column. The column was eluted with EtOAc followed by 5% MeOH/EtOAc. The product-containing fractions were pooled and evaporated in vacuo to yield 11.5 gm Boc-NMeTyr(Bzl)-D-Lys(Nic)-O-Me. FABMS: $(M+H)^+=633$

EXAMPLE 16

Boc-Ser(Bzl)-NMeTyr(Bzl)-D-Lys(Nic)-O-Me

A. Deprotection

A solution of Boc-NMeTyr(Bzl)-D-Lys(Nic)-O-Me (10 gm) in HCl/EtOAc (100 mL) was stirred for one hour at ambient temperature. The solvent was evaporated in vacuo to yield a hygroscopic oil which was dried in vacuo over NaOH pellets to yield 10 gm of the deprotected dipeptide.

B. Coupling

A stirred solution of Boc-Ser(Bzl)-OH (3.85 gm) in DCM (30 mL) was cooled in an ice bath, EDC.HCl (1.40 gm) was added, and the reaction to form the symmetric anhydride was stirred 2 hours at 0° to 5° C. In a separate flask 2HCl.NMeTyr(Bzl)-D-Lys(Nic)-O-Me from above (2.62 gm) was dissolved in DMF (20 mL) and the solution cooled to 0° to 5° C. After addition of NMM (0.95 mL), the symmetric anhydride solution was added and the reaction stirred one hour at 0° or 5° C. and then four hours at ambient temperature. The solution was concentrated in vacuo and the residue dissolved in 130 mL EtOAc. This solution was washed successively with water (85 mL), 5% NaHCO3 (2×110 mL) and water to neutral pH. The organic solution was dried over $Na_2SO_4$ and evaporated in vacuo to yield an oil. The oil was applied to a silica gel (55 gm) column and eluted successively with 80% EtOAc/heptane, 90% EtOAc/heptane and heptane. The product-containing fractions were combined and concentrated in vacuo to yield 2.19 gm Boc-Ser(Bzl)-NMeTyr(Bzl)-D-Lys(Nic)-O-Me. FABMS $(M+H)^+=810$, $(M+H-Boc)^{30}=710$

EXAMPLE 17

Boc-Ser(Bzl)-NMeTyr(Bzl)-D-Lys(Nic)-OH

The tripeptide Boc-Ser(Bzl)-NMeTyr(Bzl)-D-Lys(Nic)-O-Me (0.809 gm) was dissolved in MeOH (10 mL) and the solution cooled to 0° to 5° C. With good stirring, 1N NaOH (1 mL+0.5 mL) was added over three hours, then the pH was acidified with aqueous citric acid and the MeOH removed in vacuo. The residue was diluted with water and the pH made basic. This solution was extracted with EtOAc (2×15 mL), and the aqueous phase acidified to pH 3 with citric acid. The mixture was extracted with EtOAc (4×15 mL). The EtOAc extracts were combined and washed with water to neutral pH, and evaporated in vacuo to dryness to yield 0.52 gm of Boc-Ser(Bzl)-NMeTyr(Bzl)-D-Lys(Nic)-OH. FABMS $(M+H)^+=796.8$, $(M+H-Boc)^+=696.8$

EXAMPLE 18

2R,S-THF-Gly-O-Bzl

A stirred mixture of 2-R,S-tetrahydrofuroic acid (2R,S-THFA, 1.16 gm), glycine benzyl ester hydrochloride (2.22 gm), HOBt (2.14 gm), and THF (30 mL) was cooled to about 5° C. A two-phase mixture of EDC.HCl (2.01 gm), THF (5 mL) and water (5 mL) was added followed by NMM (1.2 mL). The reaction was stirred 20 minutes at 0° or 5° C., then warmed to ambient temperature and stirred overnight. The reaction mixture was poured into water (100 mL) and the mixture extracted with EtOAc (2×10 mL). The organic extracts were combined and washed with 5% citric acid, 10% $Na_2CO_3$ and water. The resulting EtOAc solution was concentrated in vacuo to yield 2.47 gm of 2R,S-THF-Gly-O-Bzl as a yellow oil. MS: $(M+H)^{30}=264$, $(M+NH_4)^{30}=281$

EXAMPLE 19

2R,S-THF-Gly-OH

A solution of 2R, S-THF-Gly-O-Bzl (0.80 gm) in methanol (20 mL) was hydrogenated over 5% Pd/C (0.08 gm) at 10 psi for two hours. the catalyst was filtered off and the filtrate was concentrated in vacuo to yield an oil (0.51 gm). MS: $(M+H)^+=174$, $(M+NH_4)^+=191$

EXAMPLE 20

2R-THF-Gly-O-Bzl

A stirred mixture of 2R-THFA.brucine salt (18.98 gm), glycine benzyl ester hydrochloride (HCl.Gly-O-Bzl, 13.72 gm), HOBt (7.93 gm) and THF (100 mL) was cooled to 5° C. A mixture of EDC.HCl (7.80 gm) in water (10 mL) was added followed by a water (5 mL) rinse of the EDC.HCl container. After an initial exotherm to about 11° C., the mixture was cooled to 5° C. for 10 minutes, then the cooling bath was removed and the mixture stirred overnight at ambient temperature. The reaction mixture was partitioned between EtOAc (400 mL) and 1N $H_2SO_4$. The layers were separated and the aqueous layer washed with EtOAc (300 mL). The combined organic layers were washed with 1N $H_2SO_4$ (1×200 mL), 10% $Na_2CO_3$ solution (2×200 mL) and water (2×200 mL). The resulting EtOAc solution was concentrated in vacuo to an oil, then redissolved in EtOAc (200 mL) and reconcentrated in vacuo to yield 10.32 gm of 2R-THF-Gly-O-Bzl as a yellow oil. MS: $(M+H)^+=264$, $(M+NH_4)^+=281$

EXAMPLE 21

2R-THF-Gly-OH

A solution of 2R-THF-Gly-O-Bzl (11.41 gm) in 2-propanol (90 mL) and EtOAc (10 mL) was hydrogenated over 5% Pd/C (0.52 gm) at 40 psi for 14 hours. The catalyst was filtered off and the solution was concentrated in vacuo to 32 gm. Ethyl acetate (100 m mL) was added and the solution concentrated in vacuo to 10 gm, and the residue re-dissolved in EtOAc (100 mL) and re-concentrated in vacuo to a 12.5 gm. The residue was treated with EtOAc (40 mL) and heptanes (50 mL) and the mixture heated to reflux, then cooled to 5° C. The resulting solids were filtered off and dried in vacuo to yield 4.96 gm of 2R-THF-Gly-OH. Mp: 116°–117° C. (uncorr.) MS: $(M+H)^+=174$, $(M+H_4)^+=191$

EXAMPLE 22

2S-THF-Gly-O-Bzl

A stirred mixture of 2S-tetrahydrofuroic acid (2S-THFA, 2.32 gm), glycine benzyl ester hydrochloride (HCl.Gly-O-Bzl, 4.44 gm), 1-hydroxybenzotriazole hydrate (HOBt, 4.28 gm) and tetrahydrofuran THF, 50 mL) was cooled to about 10° C. A two-phase mixture of 1-(3-dimethylaminopropyl)-3-ethylcarbodiimide hydrochloride (EDC.HCl, 4.03 gm), THF (10 mL) and water (5 mL) was added followed by N-methylmorpholine (NMM, 2.40 mL). After an initial exotherm to 12° C., the mixture was cooled to 5° C. and stirred 45 minutes, then warmed to ambient temperature and stirred overnight. The reaction mixture was partitioned between ethyl acetate (EtOAc, 100 mL) and 10% citric acid solution (50 mL). The layers were separated and the aqueous layer extracted with EtOAc (100 mL). The organic layers were combined and washed with 10% $K_2CO_3$ (1×50 mL) and water (1×50 mL). The resulting EtOAc solution was concentrated in vacuo to an oil, then redissolved in EtOAc (100 mL) and reconcentrated in vacuo to yield 5.30 gm of 2S-THF-Gly-O-Bzl as a yellow oil. MS: $(M+H)^+=224$, $(M+NH_4)^+=281$

EXAMPLE 22A

2S-THF-Gly-O-Bzl

A mixture of 2S-TFA.DCHA (18.89 gm), TsOH.Gly-O-Bzl (23.54 gm), HOBt (13.61 gm) and THF (198 mL) was stirred at ambient temperature 20 min., then cooled to 4° C. A solution of EDC.HCl (13.29 gm) in water (20 mL) was added over 3 to 5 min and the temperature of the reaction mixture rose to 12° C. The reaction mixture was stirred with cooling for 30 min., then at ambient temperature overnight. The mixture was then cooled to 5° C., filtered to remove solids, and the filter cake washed with EtOAc (220 mL). The combined filtrates were diluted with EtOAc (100 mL) and the solution concentrated in vacuo to 70 gm. This concentrate was partitioned between EtOAc (220 mL) and 10% $Na_2CO_3$. The layers were separated and the aqueous layer extracted with EtOAc (140 mL). The organic extracts were combined and washed with 1N $H_2SO_4$ (2×100 mL), 10% (100 mL) and water (2×100 mL). The EtOAc solution was concentrated in vacuo to about 30 gm, then diluted with EtOAc (100 mL) and concentrated in vacuo to dryness to yield 16.12 gm of 2S-THF-Gly-O-Bzl as a yellow oil. MS: $(M+H)^+=264$, $(M+NH_4)^+=281$

EXAMPLE 23

2S-THF-Gly-OH

A solution of 2S-THF-Gly-O-Bzl (4.51 gm) in methanol (45 mL) was hydrogenated over 5% Pd/C (0.45 gm) at 40 psi at 25° C. for 1.5 hr. The catalyst was filtered off and the filtrate was evaporated in vacuo to dryness. The residue was dissolved in EtOAc (50 mL) and the solution again evaporated in vacuo to yield 2.70 gm of a white solid. The solid (2.03 gm) was dissolved with heating on a steam bath in EtOAc (25 mL). The solution was cooled to 5° C. for 2 hours and the resulting solid filtered and washed with heptanes (50 mL), and dried in vacuo for 48 hr to yield 1.71 gm of S-THF-Gly-OH as a white solid. Mp: 95.5–96.5 (uncorr.); MS: $(M+H)^+=174$, $(M+NH_4)^+=191$

EXAMPLE 23A

2S-THF-Gly-OH

A solution of 2S-THF-Gly-O-Bzl (30.6 gm) in 2-propanol (300 mL) was hydrogenated over 5% Pd/C (0.612 gm) at 40 psi for 3.5 hours. The catalyst was filtered off and the solution was concentrated in vacuo to about 75 gm. Toluene (300 mL) was added and the solution again concentrated in vacuo to about 150 gm. Toluene (300 mL) was again added and the solution concentrated in vacuo to about 115 gm, then EtOAc (100 mL) was added and the mixture heated on a steam bath and transferred to a larger flask along with an EtOAc (15 mL) rinse. The mixture was heated to 83° C. then cooled to 10° C. and held for 30 minutes. The solids were filtered, washed with toluene (80 mL), and dried in vacuo to yield 16.25 gm of 2S-THF-Gly-OH. Mp: 116–118 (uncorr.); MS: $(M+H)^+=174$, $(M+NH_4)^+=191$

EXAMPLE 24

Boc-D-4ClPhe-D-3Pal-O-Me

A mixture of BOC-D-4ClPhe-OH (12.5 gm), HOBt (9.58 gm), 2HCl.D-3Pal-O-Me (10.55 gm) and in ACN (300 mL) was cooled to 0° to 5° C. with stirring and NMM (9.2 mL) and EDC.HCl (8.8 gm) were added. After stirring 4 hours the reaction mixture was poured into 5% $NaHCO_3$ (1.8 L) and the product precipitated. The solids were filtered and washed on the filter with water and dried in vacuo to yield 17.9 gm of BOC-D-4ClPhe-D-3Pal-O-Me. HPLC: 98.3 pa %.

EXAMPLE 25

BOC-D-2Nal-D-4ClPhe-D-3Pal-O-Me

A. Deprotection

A mixture of Boc-D-4ClPhe-D-3Pal-O-Me (14.0 gm) in 3.4N HCl/EtOAc (260 mL) was stirred at ambient temperature. After 3 minutes solution was attained, then after 20 minutes precipitate began to form. Ethyl acetate (88 mL) was added when the mixture had stirred 2 hours, and the solvent was evaporated in vacuo to about 125 mL. Ethyl acetate (176 mL) was added and the mixture again evaporated in vacuo to about 125 mL, and this procedure was repeated once and evaporation continued until a final volume of about 150 mL was attained. The mixture was cooled to 20° C., filtered, washed on the filter with EtOAc (2×80 mL) and held for further processing under a blanket of nitrogen (Section B). Yield: 5.1 gm B. Coupling The solid from above (Section A, 15.1 gm), Boc-D-2Nal-OH (9.6 gm) and HOBt (6.0 gm) were suspended in ACN (180 mL) and the mixture cooled to 5° C. N-Methylmorpholine (8.0 mL) was added and a solution was attained. To this solution was added a slurry of EDC.HCl (6.4 gm) in ACN (75 mL) and the reaction mixture stirred at about 5° C. for 35 minutes and a precipitate formed. The cooling was removed and the mixture was stirred overnight. The slurry was cooled to 5° C., stirred for 1 hour, and the precipitate filtered and washed on the filter with water (50 mL). The wetcake was slurried in ACN (140 mL) and water (140 mL) for 1 hour then filtered, washed on the filter with a mixture of ACN (140 mL) and water (140 mL), and dried in vacuo to yield 17.1 gm of Boc-D-2Nal-D-4ClPhe-D-3Pal-O-Me. MS: $(M+H)^+=659$, $(M+Na)^+=681$

EXAMPLE 26

2R,S-THF-Gly-D-2Nal-D-4ClPhe-D-3Pal-O-Me

A. Deprotection

A mixture of Boc-D-2Nal-D-4ClPhe-D-3Pal-O-Me (1.0 gm) and trifluoroacetic acid (TFA, 8 mL) in methylene chloride (DCM, 10 mL) was stirred at ambient temperature for 1.5 hours, then partitioned between EtOAc (75 mL) and 10% $Na_2CO_3$ (100 mL). The layers were separated and the aqueous layer extracted with EtOAc (75 mL). The EtOAc extracts were combined and washed with 10% $Na_2CO_3$ (50 mL) and water (50 mL) and concentrated in vacuo to dryness to yield a white solid. The solids slurried in heptanes, then filtered and the filter cake was washed with heptanes and dried on the filter to yield ca. 0.84 gm of D-2Nal-D-4ClPhe-D-3Pal-O-Me.

B. Coupling

A mixture of D-2Nal-D-4ClPHe-D-3Pal-O-Me (ca. 0.84 gm), 2R,S-THF-Gly-OH (0.29 gm), HOBt (0.34 gm) and NMP (10 mL) was stirred and cooled to in an ice-water bath. A solution of EDC (0.32 gm) in water (1 mL) was added followed by NMM (0.2 mL), and the mixture was stirred with cooling for 30 minutes followed by stirring at ambient temperature overnight. The reaction mixture was partitioned between EtOAc (100 mL) and 10% citric acid (75 mL). The layers were separated and the aqueous layer extracted with EtOAc (100 mL). The combined organic layers were washed with 10% $Na_2CO_3$ (2×100 mL) and water (2×100 mL). The organic layer was concentrated in vacuo to dryness, the residue dissolved in EtOAc and concentrated again in vacuo to dryness to yield a white solid (1.2 gm). A portion of the solid (0.5 gm) was dissolved on a steam bath in DCM (2 mL), and this solution added slowly heptanes (30 mL) and a precipitate formed. This mixture was stirred 30 minutes and the solids were filtered, washed on the filter with heptanes and dried in vacuo to yield 0.4 gm of 2R,S-THF-Gly-D-2Nal-D-4ClPHe-D-3Pal-O-Me. MS: $(M+H)^+=714$, $(M+Na)^+=736$

EXAMPLE 27

2R-THF-Gly-D-2Nal-D-4ClPhe-D-3Pal-O-Me

A. Deprotection

A solution of Boc-D-2Nal-D-4ClPHe-D-3Pal-O-Me (20 gm) and TFA (81 mL) in DCM (166 mL) was stirred one hour, then the reaction mixture was partitioned between EtOAc (600 mL) and 15% $K_2CO_3$ (100 mL). The layers were separated and the aqueous layer was extracted with EtOAc (300 mL). The EtOAc extracts were combined, washed with 15% $K_2CO_3$ (250 mL) and water (2×250 mL), and concentrated in vacuo to about 500 mL. N-Methylpyrrolidinone (120 mL) was added to the solution and the evaporation in vacuo continued until distillation ceased, then the solution was cooled to 20°±5° C.

B. Coupling

To the solution from Section A were added R-THF-Gly-OH (5.5 gm), HOBt (7.0 gm) and NMP (20 mL), and the solution cooled to 5°±5° C. A solution of EDC.HCl (6.4 gm) in water (6.4 mL) was added to the mixture followed by NMM (3.6 mL). The reaction was stirred at 5°±5° C. for 30 minutes and then at ambient temperature for 4 hours. The reaction mixture was partitioned between EtOAc (320 mL) and water (320 mL) and the layers were separated and the aqueous layer was extracted with EtOAc (430 mL). The organic extracts were combined and washed with 10% $Na_2CO_3$ (2×250 mL) and water (2×300 mL), and the solvent evaporated in vacuo to about 300 added. A portion of EtOAc (350 mL) was added and the evaporation in vacuo continued again to about 300 mL. More EtOAc (300 mL) was added along with MTBE (150 mL) and a precipitate formed. After stirring 4 hours, the solids were filtered, washed on the filter with a EtOAc (100 mL)-MTBE (100 mL) mixture, and dried in vacuo to yield 20.32 gm of 2R-THF-Gly-D-2Nal-D-4ClPHe-D-3Pal-O-Me. FABMS: $(M+H)^+=714$

EXAMPLE 28

2S-THF-Gly-D-2Nal-D-4ClPhe-D-3Pal-O-Me

A. Deprotection

A mixture of Boc-D-2Nal-D-4ClPHe-D-3Pal-O-Me (6.1 gm) and trifluoroacetic acid (TFA, 15 mL) in methylene chloride (DCM, 30 mL) was stirred at ambient temperature for 2.25 hours, then partitioned between EtOAc (200 mL) and 10% $Na_2CO_3$. The layers were separated and the aqueous layer extracted with EtOAc (200 mL). The EtOAc extracts were combined and washed with 10% $Na_2CO_3$ (100 mL) and water (100 mL) and concentrated in vacuo to dryness to yield a white solid. The solids were dissolved in DCM (40 mL) and added dropwise to heptanes (200 mL) and a precipitate formed. EtOAc (30 mL) was added to the mixture and the slurry stirred 30 minutes, then filtered and the filter cake was washed with heptanes (20 mL) and dried on the filter to yield 7.1 gm of D-2Nal-D-4ClPHe-D-3Pal-O-Me.

B. Coupling

A mixture of D-2Nal-D-4ClPhe-D-3Pal-O-Me (3.39 gm), 2S-THF-Gly-OH (1.10 gm), HOBt (1.39 gm) and N-methylpyrrolidinone (NMP, 30 mL) was stirred and cooled to 5° C. A solution of EDC (1.28 gm) in water (3 mL) was added followed by N-methylmorpholine (NMM, 0.8 mL), and the mixture was stirred at 5° C. for 30 minutes followed by stirring at ambient temperature overnight. The reaction mixture was partitioned between EtOAc (100 mL) and water (50 mL). The layers were separated and the aqueous layer extracted with EtOAc (200 mL). The combined organic layers were washed with water (50 mL), 10% $Na_2CO_3$ (2×75 mL) and water (50 mL). The organic layer was concentrated in vacuo to dryness, the residue dissolved in EtOAc and concentrated again in vacuo to dryness to yield a white solid (4.29 gm). The solid was dissolved on a steam bath in a mixture of EtOAc (35 mL) and MeOH (30 mL), and the solution added slowly to methyl t-butyl ether (MTBE, 125 mL) and a precipitate formed. This mixture was treated with MTBE (60 mL) and heptanes (80 mL), then stirred at 5° C. for one hour. The solids were filtered and dried in vacuo to yield 3.66 gm of 2S-THF-Gly-D-2Nal-D-4ClPHe-D-3Pal-O-Me. MS: $(M+H)^+=714$, $(M+Na)^+=736$

EXAMPLE 29

2R,S-THF-Gly-D-2Nal-D-4ClPHe-D-3Pal-OH

A solution of 2R,S-THF-Gly-D-2Nal-D-4ClPHe-D-3Pal-O-Me (1.0 gm) in NMP (10 mL) and water (1.0 mL) was cooled to −5° C. A solution of 1N NaOH (1.5 mL) was added and the mixture stirred at −5° to 0° C. for 2 hours. The reaction solution was added to a mixture of water (50 mL) and ACN (20 mL) and the pH adjusted to 4 with 1N HCl. After stirring overnight the resulting precipitate was filtered off and washed with water. The solids were crystallized from HOAc (3 mL) and EtOAc (20 mL) to yield 0.45 gm of 2R,S-THF-Gly-D-2Nal-D-4ClPHe-D-3Pal-OH. MS: $(M+H)^+=700$, $(M+Na)^+=722$, $(M+H+2Na)^+=744$

EXAMPLE 30

2R-THF-Gly-D-2Nal-D-4ClPhe-D-3Pal-OH

A solution of 2R-THF-Gly-D-2Nal-D-4ClPHe-D-3Pal-O-Me (10 gm) in NMP (30 mL) and THF (39 mL) was cooled to about −10° C. A solution of NaOH in water and NMP was added slowly, maintaining the temperature at −9° to −10° C. After stirring one hour at −10° C. the reaction solution was added to a cold solution of ACN (76 mL), water (260 mL) and 1N HCl (24 mL). The pH was adjusted to 4.0±0.2 and warmed to ambient temperature and a precipitate formed. After stirring overnight, the pH was again adjusted to 4.0±2 and the mixture was stirred an additional 2 hours. The solids were filtered off, washed on the filter with an ACN (40 mL)-water (60 mL) mixture and dried in vacuo at 40° C. to yield 6.7 gm of crude product. This material was dissolved in a hot mixture of water (2.4 mL), HOAc (51 mL) and EtOAc (27 mL) and filtered hot. The filtrate was treated with HOAc (10 mL) and EtOAc (300 mL) and the product began to crystallize. After stirring 5-6 hours at 10°-15° C., the solids were filtered, washed on the filter with EtOAc (2×100 mL) and dried in vacuo to yield 6.2 gm of 2R-THF-Gly-D-2Nal-D-4ClPHe-D-3Pal-OH. FABMS: $(M+H)^+=700$, $(M+K)^+=738$

EXAMPLE 31

2S-THF-Gly-D-2Nal-D-4ClPHe-D-3Pal-OH

Water (1.4 mL) was added to a solution of 2S-THF-Gly-D-2Nal-D-4ClPhe-D-3Pal-O-Me (1.40 gm) in NMP (14 mL) and the mixture stirred and cooled under a $N_2$ blanket to −18° C. A solution of 1N NaOH (2.35 mL) was added over 10 minutes and the solution stirred at −18° C. to −10° C. for 2 hours after the addition was complete. Another aliquot of 1N NaOH (0.25 mL) was added and the mixture stirred another 1.5 hours at −10° C. to −3° C. The reaction mixture was diluted with water (30 mL) and 1N HCl (2 mL), followed by acetonitrile (ACN, 10 mL). The pH of the mixture was adjusted to 4.18 with 1N HCl to give a thick precipitate. The mixture was diluted with water (10 mL) and ACN (10 mL), stirred overnight, filtered and washed on the filter with water (50 mL) to yield a white solid (1.31 gm). A portion of this solid (1.05 gm) was dissolved in acetic acid (HOAc, 9 mL) at 35° C., and the solution added to EtOAc (30 mL) at ambient temperature. Additional amounts of EtOAc (15 mL) and HOAc (2 mL) and the mixture stirred one hour, then cooled to 5° C. and stirred another hour. The solids were filtered off and dried in vacuo at 50° C. for 16 hours to yield 0.8 gm 2S-THF-Gly-D-2Nal-D-4ClPHe-D-3Pal-OH. MS: $(M+H)^+=700$, $(M+Na)^+=722$

EXAMPLE 32

Boc-Ser(Bzl)-NMeTyr(Bzl)-D-Lys(Nic)-Leu-Lys(iPr,Fmoc)-Pro-D-Ala-NH$_2$

A. Deprotection

Boc-Lys(iPr,Fmoc)-Pro-D-Ala-NH$_2$ was dissolved in EtOAc (50 mL) and added to a 2.6N HCl/EtOAc solution and stirred 45 min at ambient temperature. Ethyl acetate (100 mL) was added and the mixture concentrated in vacuo to dryness. The residue was taken up in EtOAc (200 mL) and again concentrated to about 150 mL. Heptane (a total of 300 mL) was added while concentrating until a precipitate began to form. The resulting slurry was stirred at ambient temperature 45 minutes, then filtered, washed on the filter with heptane (2×200 mL) and dried in vacuo to yield 18.0 gm HCl.Lys(iPr,Fmoc)-Pro-D-Ala-NH$_2$.

B. Coupling

The deprotected tripeptide (Section A, 1.7 gm), Boc-Ser(Bzl)-NMeTyr(Bzl)-D-Lys(Nic)-Leu-OH (2.4 gm) and 3-Hydroxy-1,2,3-benzotriazin-3(4H)-one (HOOBt, 0.54 gm) were dissolved in NMP (10 mL) and the solution cooled to 0° C. 1-(3-Dimethylaminopropyl)-3-ethylcarbodiimide hydrochloride (EDC.HCl, 0.56 gm) was added followed by NMM (0.58 gm), and the mixture stirred and allowed to warm to about 10° C. over three hours, then stirred at ambient temperature overnight. The reaction solution was added to a cold (0°-5° C.) solution of 5% $K_2CO_3$ (200 mL) over about 15 minutes and a solid precipitated. The slurry was stirred 15 minutes, then filtered and washed on the filter with water (500 mL) and dried in vacuo to yield 3.6 gm of a white-to-yellow solid. The material (3.4 gm) was purified on a silica gel (270 gm) column using a 5% to 25% step-gradient of EtOH/EtOAc in 5% increments. The product-containing fractions were combined and concentrated in vacuo to yield an oil. The oil was dissolved in EtOH (5 mL) and precipitate formed on addition to water (250 mL). The solids were filtered and dried in vacuo to yield 2.7 gm of Boc-Ser(Bzl)-NMeTyr(Bzl)-D-Lys(Nic)-Leu-Lys(iPr,Fmoc)-Pro-D-Ala-NH$_2$. MS: $(M+H)^+=1468$

EXAMPLE 32A

Boc-Ser(Bzl)-NMeTyr(Bzl)-D-Lys(Nic)-Leu-Lys(iPr,Fmoc)-Pro-D-Ala-NH$_2$

A. Deprotection

The tetrapeptide Boc-Leu-Lys(iPr,Fmoc)-Pro-D-Ala-NH$_2$ (1.0 gm) was treated with an HCl/EtOAc solution for 30 minutes, then the mixture was evaporated in vacuo to dryness. The residue was triturated with an EtOAc-ether (1:1) mixture and the residue filtered and dried in vacuo to yield 0.9 gm of HCl.Leu-Lys(iPr,Fmoc)-Pro-D-Ala-NH$_2$.

B. Coupling

A solution of HCl.Leu-Lys(iPr,Fmoc)-Pro-D-Ala-NH$_2$ (0.456 gm) in DMF (4 mL) was cooled to 0°-5° C. and NMM (69 mL), Boc-Ser(Bzl)-NMeTyr(Bzl)-D-Lys(Nic)-OH (0.5 gm), HOOBt (0. 154 gm) and THF (5 mL) were added. While stirring at 0° C., EDC.HCl (0.132 gm) was added and the mixture stirred 2 hours at 0° C. then left in at 4° C. overnight. The solvent was evaporated in vacuo and the residue partitioned between water (15 mL) and EtOAc (15 mL). The layers were separated and the aqueous layer was extracted with EtOAc (3×15 mL). The organic extracts were combined and washed with 5% citric acid (2×25 mL), water, NaHCO$_3$ (2×25 mL) and finally with water. The solvent was removed in vacuo and the residue purified on a silica gel (30 gm) column with a 0–6% MeOH/EtOAc step gradient profile with 2% increments in MeOH. The product-containing fractions were pooled and concentrated in vacuo to yield 0.7 gm of Boc-Ser(Bzl)-NMeTyr(Bzl)-D-Lys(Nic)-Leu-Lys(iPr,Fmoc)-Pro-D-Ala-NH$_2$. FABMS: $(M+H)^+=1468$, $(M+H-Boc)^+=1368$

EXAMPLE 33

Boc-Ser(Bzl)-NMeTyr(Bzl)-D-Lys(Nic)-Leu-Lys(iPr)-Pro-D-Ala-NH$_2$

A. Deprotection

A solution of 2.3N HCl/EtOAc (198 mL) was added to a solution of Boc-Lys(iPr)-Pro-D-Ala-NH$_2$ (6.0 gm) in DCM (60 mL). After stirring one hour at ambient temperature, the solution was concentrated in vacuo to about one-third volume. Ethyl acetate (100 mL) was added and the solution was again concentrated in vacuo to about one-third volume. Another portion of EtOAc (100 mL) was added and the solution evaporated in vacuo to dryness. Acetonitrile (ACN, 108 mL) and water (12 mL) were added to the residue and the mixture was stirred 10 minutes. N-Methyl-pyrrolidinone (90 mL) was added and the solution evaporated in vacuo until distillation ceased and held for the coupling step (see Section B.)

B. Coupling

To the solution above (Section A.) were added HOOBt (2.51 gm), Boc-Ser(Bzl)-NMeTyr(Bzl)-D-Lys(Nic)-Leu-OH (10.0 gm), CuCl$_2$.H$_2$O (1.14 gm) and NMP (10 mL). The mixture was stirred and cooled to 0°-5° C. and treated with NMM (4.95 mL) followed by a solution of EDC.HCl (2.64 gm) in water (5 mL). The reaction mixture was stirred overnight at ambient temperature, then partitioned between EtOAc (750 mL), ACN (55 mL), 10% NH$_4$HCO$_3$ (650 mL) and 10% K$_2$CO$_3$ (100 mL). The reaction flask was rinsed with a mixture of ACN (40 mL) and water (40 mL) and the rinse added to the partition mixture. The layers were separated and the aqueous layer extracted with EtOAc (650 mL). the organic extracts were combined and washed with 10% $NH_4HCO_3$ (200 mL) and 10% $K_2CO_3$ (100 mL). The organic layer then was extracted with 10% citric acid (3×280 mL). The citric acid extracts were combined, covered with EtOAc (650 mL) and ACN (30 mL), stirred and basified to pH 10 with 33% $K_2CO_3$ (ca. 350 mL). The layers were separated and the aqueous layer extracted with EtOAc (500 mL). The organic layers were combined and washed with 10% $K_2CO_3$ (290 mL) and water (2×290 mL), then evaporated in vacuo to dryness. Ethyl acetate (290 mL) was added to the residue and the mixture again evaporated in vacuo to dryness. The residue was taken up in EtOAc (60 mL) and added to methyl t-butyl ether (670 mL), and a precipitate formed. Heptane (380 mL) was added to the mixture and the solids filtered off and dried in vacuo to yield 11.22 gm Boc-Ser(Bzl)-NMeTyr(Bzl)-D-Lys(Nic)-Leu-Lys(iPr)-Pro-D-Ala-$NH_2$. MS: $(M+H)^+=1246$

EXAMPLE 34

Boc-Ser(Bzl)-NMeTyr(Cl Bzl)-D-Lys(Nic)-Leu-Lys(iPr)-Pro-D-Ala-$NH_2$

A. Deprotection

A solution of Lys(iPr)-Pro-D-Ala-$NH_2$ (3.03 gm) in DCM (20 mL) was added to 2.3N HCl/EtOAc (115 mL) and the mixture stirred 30 minutes at ambient temperature. Ethyl acetate (90 mL) was added and the mixture concentrated in vacuo to about 30 mL, and the residue treated with EtOAc (90 mL) and the mixture evaporated in vacuo to dryness. The gummy residue was dissolved in ACN (80 mL), water (4 mL) and NMP (36 mL) and the solution evaporated in vacuo until distillation ceased and the residue was treated with ACN (80 mL) and again evaporated in vacuo until distillation ceased. The remaining solution was held for further processing (Section B)

B. Coupling

A mixture of HOOBt (1.08 gm), $CuCl_2.H_2O$ (0.65 gm), Boc-Ser(Bzl)-NMeTyr($Cl_2$Bzl)-D-Lys(Nic)-Leu-OH (5.0 gm) NMP (18 mL) and the solution from above was cooled to 0°–5° C., and NMM (2.3 mL) was added. A solution of EDC.HCl (1.18 gm) in water (2.4 mL) was added and the reaction was stirred at 0°–5° C. for 30 minutes, then overnight at ambient temperature. The reaction solution was partitioned between a mixture of EtOAc (375 mL), 10% $NH_4HCO_3$ (320 mL), ACN (25 mL) and 10% $K_2CO_3$ (50 mL), and the layers were separated. The aqueous layer was extracted with EtOAc (325 mL), and the organic extracts were combined and washed with a mixture of 10% $NH_4HCO_3$ (200 mL) and 10% $K_2CO_3$ (50 mL). The product was extracted into 10% citric acid (2×140 mL), and the combined citric acid extracts were covered with EtOAc ((325 mL) and ACN (40 mL) and the pH of the mixture adjusted to 10 with 33% $K_2CO_3$ (230 mL). The layers were separated and the aqueous layer extracted with EtOAc (250 mL). The organic layers were combined and washed with 10% $K_2CO_3$ (140 mL) and water (2×70 mL), and evaporated in vacuo to dryness. The residue was treated with EtOAc and the mixture evaporated in vacuo to dryness, and this procedure repeated. The residue was dissolved in EtOAc (45 mL) and the solution added to a mixture of MTBE (350 mL) and heptane (175 mL) and a precipitate formed. The solids were filtered, washed on the filter with MTBE (100 mL) and dried in vacuo to yield 5.86 gm Boc-Ser(Bzl)-NMeTyr(Cl Bzl)-D-Lys(Nic)-Leu-Lys(iPr)-Pro-D-Ala-$NH_2$. MS: $(M+H)^+=1314$, $(M+K)^+=1352$.

EXAMPLE 35

2R,S-THF Gly-D-2Nal-D-4ClPhe-D-3Pal-Ser(Bzl)-NMeTyr(Bzl)-D-Lys(Nic)-Leu-Lys(iPr,Fmoc)-Pro-D-Ala-$NH_2$ A. Deprotection A slurry of Boc-Ser(Bzl)-NMeTyr(Bzl)-D-Lys(Nic)-Leu-Lys(iPr,Fmoc)-Pro-D-Ala-$NH_2$ (7.00 gm) in DCM (25 mL) was treated with TFA (25 mL) for 30 minutes. The reaction mixture was added to MTBE (420 mL), the resulting slurry treated with heptane (210 mL) and stirred another one hour. The solids were filtered and washed on the filter with heptane. The wet cake was dissolved in EtOAc (300 mL) and the solution extracted with 10% $Na_2CO_3$. The layers were separated and the aqueous layer was extracted with EtOAc (150 mL). The organic extracts were combined, washed with 10% $Na_2CO_3$ (200 mL) and water (200 mL) and evaporated in vacuo to an oil. The oil was dissolved in EtOAc (30 mL) and held for further processing (Section B).

B. Coupling

A solution of 2R,S-THF-Gly-D-2Nal-D-4ClPHe-D-3Pal-OH (3.52 gm), HOOBt (1.09 gm), $CuCl_2.H_2O$ (0.82 gm) and NMP (25 mL) was combined with the solution from Section A and the mixture cooled to 5° C. under an nitrogen blanket. A solution of EDC.HCl (1.01 gm) in water (1.5 mL) was added followed by NMM (1.16 mL), and the reaction stirred with cooling for 40 minutes then at ambient temperature 16 hours. The reaction mixture was partitioned between EtOAc (200 mL) and 10% citric acid (300 mL). The layers were separated and the aqueous layer extracted with EtOAc (200 mL). The organic layers were combined and washed successively with 10% citric acid (300 mL), 10% $Na_2CO_3$ (2×200 mL), water (150 mL), $Na_2$EDTA (150 mL) and water (150 mL), and evaporated in vacuo to dryness. The residue was taken up in EtOAc (300 mL) and the solution again evaporated in vacuo to dryness.

C. Purification

The material from Section B was applied to a silica gel (800 gm) column and the column eluted with the following solvent systems.

|   | EtOAc | MeOH | HOAc | $H_2O$ | Vol (L) |
|---|-------|------|------|--------|---------|
| A | 95    | 2    | 1    | 2      | 2       |
| B | 93    | 4    | 1    | 2      | 2       |
| C | 91    | 6    | 1    | 2      | 6       |
| D | 89    | 8    | 1    | 2      | 8       |
| E | 85    | 12   | 1    | 2      | 15      |

The product-containing fractions were combined and evaporated in vacuo to dryness. The residue was dissolved in EtOAc (400 mL) and washed with 10% $Na_2CO_3$ (200 mL, then 100 mL) and water, then evaporated in vacuo to dryness. The residue was dissolved in DCM (20 mL) and the solution added to stirred MTBE and a precipitate formed. After the addition of heptane (75 mL) the solids were filtered, washed on the filter with heptane (50 mL) and dried in vacuo to yield 8.04 gm of 2R,S-THF-Gly-D-2Nal-D-4ClPHe-D-3Pal-Ser(Bzl)-NMeTyr(Bzl)-D-Lys(Nic)-Leu-Lys(iPr,Fmoc)-Pro-D-Ala-$NH_2$. MS: $(M+H)^+=2049$

EXAMPLE 36

2R-THF-Gly-D-2Nal-D-4ClPhe-D-3Pal-Ser(Bzl)-
NMeTyr(Bzl)-D-Lys(Nic)-Leu-Lys(iPr,Fmoc)-Pro-
D-Ala-NH$_2$ A. Deprotection A solution of Boc-Ser(Bzl)-NMeTyr(Bzl)-D-Lys(Nic)-Lys(iPr,Fmoc)-Pro-D-Ala-NH$_2$ (11 gm) in DCM (33 mL) was treated with TFA (34 mL) and the mixture stirred 20 minutes. The reaction solution was partitioned between EtOAc (500 mL) and 15% K$_2$CO$_3$ (400 mL), the layers were separated, and the aqueous layer was extracted with EtOAc (300 mL). The organic layers were combined, washed with 5% NaCl (200 mL) and water (200 mL), and concentrated in vacuo to about 50 mL. Ethyl acetate (200 mL) was added and the solution again concentrated in vacuo to about 25 mL and held for further processing (Section B).

B. Coupling

To the solution from above were added HOOBt (1.43 gm), CuCl$_2$.H$_2$O (0.957 gm), 2R-THF-Gly-D-2Nal-D-4ClPHe-D-3Pal (5.72 gm) and NMP (44 mL). After stirring 15 minutes, all materials dissolved and the solution was cooled to 0°±5° C. A solution of EDC-HCl (1.65 gm) in H$_2$O 1.65 mL) was added to the reaction mixture followed by NMM (1.65 mL). The reaction was stirred at 0°–5° C. 30 minutes, then at ambient temperature overnight. The reaction mixture was partitioned between EtOAc (500 mL) and 10% NH$_4$HCO$_3$ (250 mL), the layers were separated, and the aqueous layer extracted with EtOAc (400 mL). The organic layers were combined and washed with 10% NH$_4$HCO$_3$ (160 mL), 10% Na$_2$CO$_3$ (160 mL), 10% NaCl (170 mL) and water (150 mL). The EtOAc solution was evaporated in vacuo to dryness to yield an oil.

C. Purification

The oil from Section B was dissolved in DCM (45 mL), applied to a silica gel (825 gm), and the column eluted with the following solutions:

| | EtOAc | MeOH | H$_2$O | HOAc | Vol (L) |
|---|---|---|---|---|---|
| A | 93 | 4 | 1 | 2 | 2 |
| B | 89 | 8 | 1 | 2 | 4 |
| C | 85 | 12 | 1 | 2 | 16 |

The product-containing fractions were combined and concentrated in vacuo to a volume of about 200 mL. The residue was diluted with EtOAc (400 mL) and then washed with 0.5% NaCl (2×200 mL), 10% Na$_2$CO$_3$ (350 mL) and water (2×200 mL) until the pH was neutral. The solution was concentrated in vacuo to about 200 mL, then treated with EtOAc (350 mL) and again evaporated in vacuo to about 200 mL and when this procedure was repeated material began to separate out when the volume reached about 200 mL. Methanol (5 mL) was added and the solution was added slowly to MTBE (800 mL) and a precipitate formed. The solids were filtered, washed on the filter with heptane, and dried in vacuo to yield 12.55 gm 2R-THF-Gly-D-2Nal-D-4ClPHe-D-3Pal-Ser(Bzl)-NMeTyr(Bzl)-D-Lys(Nic)-Leu-Lys(iPr,Fmoc)-Pro-D-Ala-NH$_2$. ESIMS=2049.7

EXAMPLE 37

2S-THF-Gly-D-2Nal-D-4ClPHe-D-3Pal-Ser(Bzl)-
NMeTyr(Bzl)-D-Lys(Nic)-Leu-Lys(iPr,Fmoc)-Pro-
D-Ala-NH$_2$ A. Deprotection Trifluoroacetic acid (30 mL) was added to a solution of Boc-Ser(Bzl)-NMeTyr(Bzl)-D-Lys(Nic)-Leu-Lys(iPr,Fmoc)-Pro-D-Ala-NH$_2$ (10.0 gm) in DCM (30 mL). After stirring 30 minutes, the mixture was partitioned between 10% K$_2$CO$_3$ (300 mL) and EtOAc (500 mL). The layers were separated and the organic layer was washed with water (200 mL) and evaporated in vacuo to dryness to yield an oil. The oil was taken up in EtOAc (20 mL) and held for further processing (Section B).

B. Coupling

A solution of HOOBt (1.33 gm), CuCl$_2$.2H$_2$O (0.54 gm), 2S-THF-Gly-D-2Nal-D-4ClPHe-D-3Pal-OH (5.24 gm), the solution from Section A, and EtOAc (5 mL) was stirred and cooled to 5°±5° C. The mixture was treated with a solution of NMM (1.65 mL) and NMP (1.7 mL), followed by a solution of EDC.HCl (1.41 gm) in water (1.40 mL), and stirred 30 minutes at 5°±5° C. The cooling was removed and the reaction mixture stirred another 3.5 hours. The reaction mixture was diluted with NMP (30 mL) then partitioned between EtOAc (500 mL) and 10% citric acid (160 mL). An NMP rinse (20 mL) of the reaction flask was also added to the partition mixture. The layers were separated and the aqueous layer extracted with EtOAc (500 mL), the combined organic layers were washed with 10% citric acid (160 mL), 1% EDTA (160 mL), 15% K$_2$CO$_3$ (2×160 mL) and 0.5% NaCl (160 mL). The resulting EtOAc solution was evaporated in vacuo to yield an oil.

C. Purification

The oil was dissolved in DCM (10 mL) and purified on a silica gel (1700 gm) column with the following step gradient profile:

| | EtOAc | MeOH | H$_2$O | HOAc | Vol (L) |
|---|---|---|---|---|---|
| A | 93 | 4 | 1 | 2 | 4 |
| B | 89 | 8 | 1 | 2 | 4 |
| C | 87 | 10 | 1 | 2 | 8 |
| D | 85 | 12 | 1 | 2 | 26 |

The product-containing fractions were combined and evaporated in vacuo to dryness. The resulting oil was dissolved in EtOAc (600 mL) and the solution was washed with 0.5% NaCl (2×200 mL), 15% K$_2$CO$_3$ (200 mL) and water (200 mL) and evaporated in vacuo to dryness. The resulting oil was dissolved in EtOAc (120 mL) and MeOH (4 mL) and added to MTBE (500 mL) and a precipitate formed. Heptane (500 mL) was added and the slurry stirred for 15 minutes, then filtered and dried in vacuo to yield 10.7 gm 2S-THF-Gly-D-2Nal-D-4ClPHe-D-3Pal-Ser(Bzl)-NMeTyr(Bzl)-D-Lys(Nic)-Leu-Lys(iPr,Fmoc)-Pro-D-Ala-NH$_2$.

EXAMPLE 38

2R-THF-Gly-D-2Nal-D-4ClPhe-D-3Pal-Ser(Bzl)-
NMeTyr(Bzl)-D-Lys(Nic)-Leu-Lys(iPr)-Pro-D-Ala-
NH$_2$

A solution of 2R,S-THF-Gly-D-2Nal-D-4ClPHe-D-3Pal-Ser(Bzl)-NMeTyr(Bzl)-D-Lys(Nic)-Leu-Lys(iPr,Fmoc)-Pro-D-Ala-NH$_2$ (10.5 gm) in NMP (60 mL) was treated with piperidine (12 mL) and the solution stirred at ambient temperature for one hour. The reaction mixture was partitioned between 20% citric acid (400 mL) and EtOAc (400 mL), the layers were separated, and the organic layer was extracted with 20% citric acid (400 mL). The aqueous layers were combined and the pH adjusted to 11 with 33% $K_2CO_3$ solution, and the resulting mixture was extracted with EtOAc (3×400 mL). The EtOAc extracts were combined, washed with water (2×250 mL) and evaporated in vacuo to dryness. The residue was taken up in EtOAc and again evaporated in vacuo to dryness. Finally, the residue was dissolved in EtOAc (25 mL) and MeOH (5 mL), and the solution added slowly to MTBE (1.2 L) and a precipitate formed. The solids were faltered, washed on the filter with MTBE, and dried in vacuo to yield 9.1 gm of 2R,S-THF-Gly-D-2Nal-D-4ClPHe-D-3Pal-Ser(Bzl)-NMeTyr(Bzl)-D-Lys(Nic)-Leu-Lys(iPr)-Pro-D-Ala-$NH_2$. ESIMS=1827.8 (1828.6)

EXAMPLE 39

2R-THF-Gly-D-2Nal-D-4ClPHe-D-3Pal-Ser(Bzl)-NMeTyr(Bzl)-D-Lys(Nic)-Leu-Lys(iPr)-Pro-D-Ala-$NH_2$

A solution of 2R-THF-Gly-D-2Nal-D-4ClPHe-D-3Pal-Ser(Bzl)-NMeTyr(Bzl)-D-Lys(Nic)-Leu-Lys(iPr,Fmoc)-Pro-D-Ala-$NH_2$ (10.5 gm) in NMP (60 mL) was purged with nitrogen, then piperidine (12 mL) was added and the solution stirred for one hour. The reaction mixture was partitioned between EtOAc (300 mL) and 20% citric acid (400 mL). The layers were separated and the organic layer extracted once with 20% citric acid (400 mL). The aqueous extracts were combined, the pH adjusted to 11 with 33% $K_2CO_3$, and extracted with EtOAc (3×300 mL). The combined EtOAc extracts were washed with water (2×200 mL) and evaporated in vacuo to yield a gum. The gum was treated with EtOAc and the mixture again evaporated in vacuo to dryness. The residue was taken up in EtOAc (25 mL) and MeOH (5 mL) and added dropwise to MTBE (1 L) and a precipitate formed. The solids were filtered and dried in vacuo to yield 8.70 gm of 2R-THF-Gly-D-2Nal-D-4ClPHe-D-3Pal-Ser(Bzl)-NMeTyr(Bzl)-D-Lys(Nic)-Leu-Lys(iPr)-Pro-D-Ala-$NH_2$. MS: $(M+H)^+$=1827

EXAMPLE 40

2 S-THF-Gly-D-2Nal-D-4ClPHe-D-3Pal-Ser(Bzl)-NMeTyr(Bzl)-D-Lys(Nic)-Leu-Lys(iPr)-Pro-D-Ala-$NH_2$

A. Deprotection

A solution of Boc-Ser(Bzl)-NMeTyr(Bzl)-D-Lys(Nic)-Leu-Lys(iPr)-Pro-D-Ala-$NH_2$ (4.28 gm) in DCM (16 mL) and TFA (16 mL) was stirred 25 minutes then partitioned between EtOAc (220 mL), ACN (20 mL) and 17% $K_2CO_3$ (280 mL). The reaction flask was rinsed with EtOAc (10 mL) and the rinse added to the partition mixture. The layers were separated and the aqueous layer extracted with EtOAc (120 mL). The organic extracts were combined and washed with water (100 mL) and 0.5% NaCl (50 mL) and evaporated in vacuo to dryness. The residue was dissolved in EtOAc (50 mL) and ACN (50 mL) and again evaporated in vacuo to dryness, the residue dissolved in NMP (15 mL) and held for further processing in section B.

B. Coupling

A mixture of 2S-THF-Gly-D-2Nal-D-4ClPHe-D-3Pal-OH (2.40 gm), HOOBt (0.78 gm), $CuCl_2 \cdot 2H_2O$ (0.44 gm) and NMP (16 mL) was stirred one hour until the solids dissolved. The solution from above (Section A) was added along with an NMP (4 mL) rinse and the solution stirred 25 minutes at ambient temperature. The solution was then cooled to 0–5° C. and stirred for 20 minutes, then 2,4,6-collidine (1.1 mL) was added and the solution stirred another 20 minutes at 0°–5° C. A mixture of EDC.HCl (0.82 gm) in water (1.25 mL) was added dropwise followed by a water rinse (0.2 mL), then the reaction mixture was stirred with cooling 90 minutes, then allowed to stand at ca. 5° C. overnight. The mixture was then warmed to ambient temperature and stirred another 2 hours. The mixture was partitioned between EtOAc (340 mL), ACN (20 mL), 17% $K_2CO_3$ (60 mL) and $NH_4HCO_3$ (140 mL), and a rinse of the reaction flask with EtOAc (10 mL) and ACN (10 mL) was added to the partition mixture. The layers were separated and the aqueous layer extracted with EtOAc (120 mL). The organic extracts were combined and washed with a mixture of 17% $K_2CO_3$ (60 mL) and $NH_4HCO_3$ (140 mL), 17% $K_2CO_3$ (200 mL), and water (120 mL). The solution was evaporated in vacuo to dryness, the concentrate dissolved in EtOAc (50 mL) and ACN (50 mL) and again evaporated in vacuo to dryness. The residue was dissolved in EtOAc (12 mL), MeOH (4 mL) and HOAc (1 mL) and held for purification (Section C).

C. Purification

A column of silica gel (320 gm) was eluted with EtOAc (1 L), then the solution from Section B was loaded and the column was eluted with the following solvent mixtures:

|   | EtOAc | MeOH | HOAc | Vol (L) |
|---|-------|------|------|---------|
| A | 1300  | 165  | 165  | 1.63    |
| B | 1135  | 325  | 165  | 1.63    |
| C | 920   | 520  | 165  | 9.36    |

The product-containing fractions were combined and evaporated in vacuo to dryness, and the residue dissolved in EtOAc (380 mL) and ACN (60 mL). The solution was treated with 17% $K_2CO_3$ (250 mL) to pH>10 and the layers were separated. The aqueous layer was washed with EtOAc (200 mL) and the combined organic extracts were washed with 17% $K_2CO_3$ (150 mL) and water (100 mL then 50 mL), and concentrated in vacuo to dryness. The residue was treated with EtOAc and again concentrated in vacuo to dryness. This residue was dissolved in EtOAc (16 mL) and MeOH (4 mL) and added dropwise to MTBE (360 mL). The precipitate was filtered and dried in vacuo to yield 5.54 gm of 2S-THF-Gly-D-2Nal-D- 4ClPHe-D-3Pal-Ser(Bzl)-NMeTyr(Bzl)-D-Lys(Nic)-Leu-Lys(iPr)-Pro-D-Ala-$NH_2$. MS: $(M+H)^+$=1827

EXAMPLE 41

2S-THF-Gly-D-2Nal-D4ClPHe-D-3Pal-Ser(Bzl)-NMeTyr(Cl Bzl)-D-Lys(Nic)-Leu-Lys(iPr)-Pro-D-Ala-$NH_2$

A. Deprotection

A solution of Boc-Ser(Bzl)-NMeTyr(Cl Bzl)-D-Lys(Nic)-Leu-Lys(iPr)-Pro-D-Ala-$NH_2$ (4.51 gm) in DCM (16 mL) was treated with TFA (16 mL) for 25 minutes. The reaction was quenched in a mixture of EtOAc (220 mL), ACN (20 mL) and 17% $K_2CO_3$ (280 mL), the layers were separated, and the aqueous layer was extracted with EtOAc (120 mL). The organic layers were combined, washed with 17% $K_2CO_3$ (100 mL) and 1% NaCl (2×50 mL), and evaporated in vacuo to dryness. The residue was dissolved in EtOAc (50 mL) and ACN (50 mL) and again evaporated in vacuo to dryness. The resulting oil was dissolved in NMP, purged with nitrogen, and held for later use (Section B).

B. Coupling

A solution of S-THF-Gly-D-2Nal-D-4ClPHe-D-3Pal-OH (2.40 gm), HOOBt (0.78 gm), CuCl$_2$.2H$_2$O (0.44 gm) and NMP (16 mL) was purged with nitrogen, then combined with the solution from Section A. The mixture was cooled to 0°–5° C. and 2,4,6-collidine (1.1 mL) and a solution of EDC.HCl (0.82 gm) in water (0.25 mL) was added and the mixture stirred at 0°–10° C. for 4 hours, followed by stirring overnight at ambient temperature under nitrogen. The reaction mixture was partitioned between EtOAc (340 mL), ACN (20 mL), 17% K$_2$CO$_3$ (60 mL) and 10% NH$_4$HCO$_3$ (140 mL). The layers were separated and the aqueous layer was extracted with EtOAc (120 mL). The organic layers were combined and washed with a mixture of 10% NH$_4$HCO$_3$ (140 mL) and 17% K$_2$CO$_3$ (60 mL), followed by 17% K$_2$CO$_3$ (200 mL). The product was extracted into 20% citric acid (2×100 mL), and the citric acid extracts combined and treated with activated carbon (0.6 gm) and celite (2 gm). The mixture was faltered through a bed of celite and filter bed washed with 20% citric acid (20 mL). The combined filtrates were covered with EtOAc (380 mL) and ACN (60 mL) and the pH adjusted to 13 with 33% K$_2$CO$_3$ (490 mL). The layers were separated and the organic layer was washed with 17% K$_2$CO$_3$ (150 mL) and water (100 mL, then 50 mL), and evaporated in vacuo to dryness. The residue was treated with EtOAc (70 mL) and again evaporated in vacuo to dryness. The residue was dissolved in MeOH (4 mL) and EtOAc (16 mL) and this solution added to MTBE (360 mL) to precipitate the product. The solids were filtered, washed on the filter with MTBE (2×40 mL) and dried in vacuo to yield 6.00 gm of 2S-THF-Gly-D-2Nal-D-4ClPHe-D-3Pal-Ser(Bzl)-NMeTyr(Cl2Bzl)-D-Lys(Nic)-Leu-Lys(iPr)-Pro-D-Ala-NH$_2$. MS: (M+H)=1895.

EXAMPLE 42

2R,S-THF-Gly-D-2Nal-D-4ClPHe-D-3Pal-Ser-NMeTyr-D-Lys(Nic)-Leu-Lys(iPr)-Pro-D-Ala-NH$_2$

A. Fmoc Deprotection

A solution of 2R,S-THF-Gly-D-2Nal-D-4ClPHe-D-3Pal-Ser(Bzl)-D-Lys(Nic)-Leu-Lys(iPr,Fmoc)-Pro-D-Ala-NH$_2$ (9.35 gm) in NMP (60 mL) was treated with Piperidine (2.60 mL) and the solution stirred at ambient temperature for one hour. The reaction mixture was partitioned between 20% citric acid (350 mL) and EtOAc (300 mL), the layers were separated, and the organic layer was extracted with 20% citric acid (350 mL). The aqueous layers were combined and the pH adjusted to 11 with 33% K$_2$CO$_3$ (850 mL), and the resulting mixture was extracted with EtOAc (3×300 mL). The EtOAc extracts were combined, washed with water (2×200 mL) and evaporated in vacuo to dryness. The residue was dissolved in EtOAc (40 ML) and MeOH (10 mL), and the solution added slowly to MTBE (1000 mL) and a precipitate formed. The solids were filtered, washed on the filter with MTBE, and dried in vacuo to yield 7.62 gm of 2R,S-THF-Gly-D-2Nal-D-4ClPHe-D-3pal-Ser(Bzl)-NMeTyr(Bzl)-D-Lys(Nic)-Leu-Lys(iPr)-Pro-D-Ala-NH$_2$.

B. Benzyl Deprotection

A solution of 2R,S-THF-Gly-D-2Nal-D-4ClPhe-D-3Pal-Ser(Bzl)-NMeTyr(Cl$_2$Bzl)-D-Lys(Nic)-Leu-Lys(iPr)-Pro-D-Ala-NH$_2$ (7.0 gm), thioanisole (16.0 gm) and TFA (56 mL) was stirred one hour at ambient temperature, then cooled to 0°–5° C. and trimethylsilyl trifluoromethanesulfonate (TMSOTf, 16.0 mL) was added and the mixture stirred 75 minutes. The reaction was then quenched in a mixture of NH$_4$OAc (152 gm), water (827 mL) and EtOAc (190 mL), and the layers separated. The organic layer was extracted with EtOAc (2×200 mL), and the organic extracts were combined and evaporated in vacuo to dryness to yield an oil.

C. Ion-exchange Chromatography #1

The residue from above was dissolved in MeOH (125 mL) and water (45 mL), the pH of the solution adjusted to 5.5 with NH$_4$OH, then adsorbed on an Amberlyte CG-50 (350 gm) column. The column was eluted successively with 75% MeOH (5 L), MeOH (5 L), 4% HOAc/MeOH (3 L) and 8% HOAc/MeOH (4 L). The product-containing fractions were combined and evaporated in vacuo to an oil.

D. C-18 Reverse Phase Chromatography

The oil from above was dissolved in MeOH (22 mL) and water (14 mL) and applied to a C-18 reverse phase (240 gm) column. The column was eluted with an ACN/water/TFA—22.5/77.5/0.1 mixture. The product containing fractions were combined and concentrated in vacuo to remove acetonitrile.

E. Ion-exchange Chromatography #2

The pH of the solution (from Section D) was adjusted to 6.8–7.1 and passed through an Amberlyte XAD-16 (475 gm) column to absorb the product. The column was washed successively with 20% NH$_4$OAc (1.5 L) and water (2.5 L), then the product was eluted with a 0.25% AcOH/MeOH solution. The product-containing fractions were combined and evaporated in vacuo to dryness to yield an oil.

F. Silica Gel Chromatography

The oil from Section E was dissolved in EtOAc (~15 mL) and applied to a silica gel (700 gm) column. The column was eluted with the following solvents:

|   | EtOAc | EtOH | HOAc | Vol (L) |
| --- | --- | --- | --- | --- |
| A | 500 | 500 | 100 | 3 |
| B | 350 | 650 | 100 | 3 |
| C | 200 | 800 | 100 | 3 |

The product-containing fractions were combined and evaporated in vacuo to dryness.

G. Ion-exchange Chromatography #3

The residue from above (Section F) was dissolved in water (2 L), the pH adjusted to 6.8–7.0 with NH$_4$OH, and the solution passed through the XAD-16 column (Section D) to absorb the product. The column was then washed successively with 20% NH$_4$OAc (1.5 L) and water (4 L) and eluted from the column with 0.25% HOAc/MeOH. The product-containing fractions were combined, evaporated in vacuo to dryness and lyophilized from acetic acid to yield 3.05 gm of 2R,S-THF-Gly-D-2Nal-D-4ClPhe-D-3Pal-Ser-NMeTyr-D-Lys(Nic)-Leu-Lys(iPr)-Pro-D-Ala-NH2. FABMS=(M+H)+ =1647 (calc 1646.8), Sequence by FABMS=THF-Gly-D-2Nal-D-4ClPHe-D-3Pal-Ser- NMeTyr-D-Lys(Nic )-Leu-Lys(iPr)-Pro-D-Ala-NH$_2$.

EXAMPLE 43

2R-THF-Gly-D-2Nal-D-4ClPHe-D-3Pal-Ser-NMeTyr-D-Lys(Nic)-Leu-Lys(iPr)-Pro-D-Ala-NH$_2$

A. Deprotection

A solution of 2R-THF-Gly-D-2Nal-D-4ClPHe-D-3Pal-Ser(Bzl)-NMeTyr(Bzl)-D-Lys(Nic)-Leu-Lys(iPr)-Pro-D-Ala-NH$_2$ (8.0 gm), 2,3,6-trimethylphenol (TMP, 16.0 gm) and TFA (56 mL) was stirred one hour at ambient temperature, then cooled to 0°–5° C. and trimethylsilyl trifluoromethanesulfonate (TMSOTf, 16.0 mL) was added and the mixture stirred 75 minutes. The reaction was quenched in a mixture of MeOH (400 mL), water (650 mL) and conc. NH$_4$OH (56 mL) at 0°–5° C. The solution was then extracted with 20%(v/v) EtOAc/heptane (3×300 mL) and heptane (2×200 mL), and the pH of the aqueous phase adjusted to 6.9±0.1.

B. Ion-exchange Chromatography #1

The solution from above (Section A) was absorbed onto an ion exchange column of Amberlyte XAD-16 (500 gm). The column was washed successively with 10% NH$_4$OAc (1450 mL), water (2900 mL), 10% NH$_4$OAc (1450 mL), water (2900 mL) and 50% MeOH (2000 mL). The product was eluted with 0.025% HOAc/MeOH and the product-containing fractions combined and evaporated in vacuo to yield a yellow oil.

C. C-18 Reverse Phase Chromatography

The residue from above (Section B) was dissolved in MeOH (6 mL) and water (3 mL) and applied to a column of C-18 reverse phase resin (145 gm) which had been equilibrated with a 20/80/0.1 (v/v) ACN/water/TFA (20% ACN) mixture. The column was eluted successively with 20% ACN and 25% ACN mixtures. The product-containing fractions were combined and held for further processing (Section D)

D. Ion-exchange Chromatography #2

The solution from above (Section C) was absorbed on a column Amberlyte CG-50 (146 gm), and the column washed successively with 50% MeOH (1500 mL) and MeOH (1500 mL). The product was eluted with a 4%(v/v) HOAc/MeOH solution and the product-containing fractions were combined and concentrated in vacuo to dryness. The residue was taken up in glacial acetic acid and lyophilized to yield 6.73 gm of 2R-THF-Gly-D-2Nal-D-4ClPHe-D-3Pal-Ser-NMeTyr-D-Lys(Nic)-Leu-Lys(iPr)-Pro-D-Ala-NH$_2$. FABMS=(M+H)$^+$=1647 (calc 1646.8). [a]D=−39.8 (c=0.5, HOAc), Elemental analysis found: C 58.12, H 6.68, N 11.82, Cl 2.03, calculated C 58.63, H 6.85, N 11.94, Cl 1.89.

EXAMPLE 44

2S-THF-Gly-D-2Nal-D-4ClPhe-D-3Pal-Ser-NMeTyr-D-Lys(Nic)-Leu-Lys(iPr)-Pro-D-Ala-NH$_2$

A. Deprotection

A solution of 2S-THF-Gly-D-2Nal-D-4ClPHe-D-3Pal-Ser(Bzl)-NMeTyr(Bzl)-D-Lys(Nic)-Leu-Lys(iPr)-Pro-D-Ala-NH$_2$ (5.0 gm), 2,3,6-trimethylphenol (TMP, 10 gm) and TFA (35 mL) was stirred one hour at ambient temperature, then cooled to 0°–5° C. and trimethylsilyl trifluoromethanesulfonate (TMSOTf, 10 mL) was added and the mixture stirred 75 minutes. The reaction was quenched in a mixture of MeOH (350 mL), water (350 mL) and conc. NH$_4$OH (36 mL) at 0°–5° C. The solution was then extracted with 10%(v/v) EtOAc/heptane (3×250 mL.

B. Ion-exchange Chromatography #1

The solution from above (Section A) was absorbed onto an ion exchange column of Amberlyte CG-50 (100), and the column washed with 75%(v/v) MeOH/water (1 L) and MeOH (1 L). The product was eluted with 5% (v/v) HOAc/MeOH (2 L) and the product-containing fractions combined and concentrated in vacuo to yield a yellow oil.

C. C-18 Reverse Phase Chromatography

The residue from above (Section B) was dissolved in MeOH (10 mL) and applied to a column of C-18 reverse phase resin (182 gm) which had been equilibrated with a 22.5/77.5/0.1 (v/v) ACN/water/TFA (22.5% ACN) mixture. The column was eluted successively with 22.5% ACN, 25% ACN and 27.5% ACN mixtures. The product-containing fractions were combined and evaporated in vacuo to remove the acetonitrile, and then the pH of the solution was adjusted to 6.9 with NH$_4$OH.

D. Ion-Exchange Chromatography #2

The solution from above (Section C) was absorbed on a column Amberlyte XAD-16 (160 gm), and the column washed successively with 17%(w/w) NH$_4$OAc (1.2 L), 0.05% NH$_4$OH (1 L), 17%(w/w) NH$_4$OAc (1.2 L) and 0.05% NH$_4$OH (2 L). The product was eluted with a 0.25%(v/v) HOAc/MeOH solution and the product-containing fractions were combined (ca. 1900 mL) and diluted with water (600 mL).

E. Ion-exchange Chromatography #3

The solution from above (Section D) was absorbed onto a second Amberlyte CG-50 (100 gm) column, and the column washed with MeOH (1 L). The product was then eluted with a 4%(v/v) HOAc/MeOH solution, and the product-containing fractions were combined and concentrated in vacuo to dryness. The residue was taken up in glacial acetic acid and lyophilized to yield 4.1 gm of 2S-THF-Gly-D-2Nal-D-4ClPhe-D-3Pal-Ser-NMeTyr-D-Lys(Nic)-Leu-Lys(iPr)-Pro-D-Ala-NH$_2$. FABMS=(M+H)+ =1647 (calc 1646.8). [a]D=−53.2 (c=0.5, HOAc).

EXAMPLE 44A

2S-THF-Gly-D-2Nal-D-4ClPhe-D-3Pal-Ser-NMeTyr-D-Lys(Nic)-Leu-Lys(iPr)-Pro-D-Ala-NH$_2$

A. Deprotection

A solution of 2S-THF-Gly-D-2Nal-D-4ClPHe-D-3Pal-Ser(Bzl)-NMeTyr(Cl Bzl)-D-Lys(Nic)-Leu-Lys(iPr)-Pro-D-Ala-NH$_2$ (2.0 gm), 2,3,6-trimethylphenol (TMP, 4.0 gm) and TFA (14 mL) was stirred one hour at ambient temperature, then cooled to 0°–5° C. and trimethylsilyl trifluoromethanesulfonate (TMSOTf, 4.0 mL) was added and the mixture stirred 75 minutes. The reaction was quenched in a mixture of MeOH (100 mL), water (150 mL) and conc. NH$_4$OH (14 mL) at 0°–5° C. The solution was then extracted with 20%(v/v) EtOAc/heptane (3×80 mL) and heptane (80 mL), and the pH of the aqueous phase adjusted to 6.9±0.1.

B. Ion-exchange Chromatography #1

The solution from above (Section A) was absorbed onto an ion exchange column of Amberlyte XAD-16 (125 gm), and the column washed with a 10% EDTA (pH adjusted to 6.9, 198 mL). The column was washed successively with water (260 mL), 10% NH$_4$OAc (825 mL), water (750 mL), 10% NH$_4$OAc (825 mL), water (825 mL) and 50% MeOH (500 mL). The product was eluted with 0.1%HOAc/MeOH and the product-containing fractions combined and evaporated in vacuo to yield a yellow oil.

C. C-18 Reverse Phase Chromatography

The residue from above (Section B) was dissolved in MeOH (6 mL) and water (3 mL) and applied to a column of C-18 reverse phase resin (37 gm) which had been equilibrated with a 20/80/0.1 (v/v) ACN/water/TFA (20% ACN) mixture. The column was eluted successively with 20% ACN and 25% ACN mixtures. The product-containing fractions were combined and held for further processing (Section D)

D. Ion-Exchange Chromatography #2

The solution from above (Section C) was absorbed on a column Amberlyte CG-50 (40 gm), and the column washed successively with 50% MeOH (500 mL) and MeOH (500 mL). The product was eluted with a 4%(v/v) HOAc/MeOH solution and the product-containing fractions were combined and concentrated in vacuo to dryness. The residue was taken up in glacial acetic acid and lyophilized to yield 1.68 gm of 2S-THF-Gly-D-2Nal-D-4ClPHe-D-3Pal-Ser-NMeTyr-D-Lys(Nic)-Leu-Lys(iPr)-Pro-D-Ala-NH$_2$. MS: (M+H)$^+$=1647

EXAMPLE 44B

2S-THF-Gly-D-2Nal-D-4ClPHe-D-3Pal-Ser-NMeTyr-D-Lys(Nic)-Leu-Lys(iPr)-Pro-D-Ala-NH$_2$

A. Deprotection

A solution of Boc-Ser(Bzl)-NMeTyr(Bzl)-D-Lys(Nic)-Leu-Lys(iPr)-Pro-D-Ala-NH$_2$ (1.0 gm) and TMP (2.0 gm) in TFA (7 mL) was cooled to 0°–5° C. and TMSOTf (2.0 mL) was added. The reaction mixture was stirred at 0°–5° C. 75 minutes and was then added to a mixture MeOH (75 mL), water (75 mL) and NH$_4$OH (7 mL). This solution was extracted with 20%(v/v) EtOAc/heptane (3×50 mL) and heptane (2×50 mL). The pH of the aqueous layer was adjusted to 7 with NH$_4$OH and absorbed on a column of Amberlyte XAD-16 (60 gm). The column was washed successively with 17% NH$_4$OAc(w/w) (338 mL), 0.05% NH$_4$OH (400 mL), 17% NH$_4$OAc(w/w) (338 mL), 0.05% NH$_4$OH (400 mL), and finally 50%(v/v) MeOH/water (200 mL). The product was then eluted with MeOH, and the product-containing fractions were combined and evaporated in vacuo to dryness to yield 0.83 gm of H-Ser-NMeTyr-D-Lys(Nic)-Leu-Lys(iPr)-Pro-D-Ala-NH$_2$ as an oil which was held for further processing. (Section B).

B. Coupling

A solution of the deprotected heptapeptide (Section A, 0.83 gm), HOOBt (0.183 gm), 2S-THF-Gly-D-2Nal-D-4ClPHe-D-3Pal-OH (0.561 gm) and CuCl$_2$.2H$_2$O (0.1025 gm) in NMP (15 mL) was cooled to 0°–5° C. and 2,4,6-collidine (0.45 mL) was added followed by a solution of EDC.HCl (0.1922 gm) in NMP (5 mL). The reaction was stirred at 0°–5° C. for seven hours and held at the same temperature overnight. The reaction mixture was diluted with 50% MeOH/water (100 mL) and filtered to remove solids.

C. Ion-Exchanger Chromatography #1

The pH of the solution was adjusted to 7–8 with NH$_4$OH and percolated through the Amberlyte XAD-16 used in Section A and the peptide absorbed onto the column. The column was washed successively with 0.025% NH$_4$OH (400 mL), 5%(w/w) (NH$_4$)$_2$EDTA adjusted to pH 7 with NH$_4$OH (210 mL), 0.033% NH$_4$OH (300 mL), 11%(w/w) NH$_4$OAc (300 mL), 0.025% NH$_4$OH (400 mL), 50%(v/v) MeOH/water (300 mL). The product was eluted with MeOH (500 mL) followed by 1% HOAc/MeOH (700 mL). The product-containing fractions were combined and evaporated in vacuo to dryness to yield a yellow-orange oil.

C. C-18 Reverse Phase Chromatography

The residue from above (Section B) was dissolved in MeOH (4 mL) and water (2 mL) and applied to a C18 reverse phase column (37 gm). The column was eluted with a ACN/water/HOAc 20/80/0.1 (v/v) mixture (500 mL) followed by a ACN/water/HOAc 25/75/0.1 (v/v) mixture. The product-containing fraction were held for further processing (Section D).

D. Ion-Exchange Chromatography #2

The solution from above (Section C) was eluted through an Amberlyte CG-50 column (30 gm) and the product adhered. The column was washed with 50% (v/v) MeOH/water (400 mL) followed by MeOH (500 mL). The product was eluted with 4% AcOH/MeOH and the product-containing fractions pooled and evaporated in vacuo to dryness to yield a pale yellow oil. The oil was dissolved in HOAc and lyophilized to yield 0.80 gm: 2S-THF-Gly-D-2Nal-D-4ClPhe-D-3Pal-Ser-NMeTyr-D-Lys(Nic)-Leu-Lys(iPr)-Pro-D-Ala-NH$_2$. FABMS (M+H)$^+$=1647 (calc 1646.8)

EXAMPLE 45

Ac-2Nal-D-4ClPHe-D-3Pal-Ser(Bzl)-NMeTyr(CL$_2$Bzl)-D-Lys(Nic)-Leu-Lys(iPr)-Pro-D-Ala-NH$_2$

A. Deprotection

A solution of Boc-Ser(Bzl)-NMeTyr(Cl Bzl)-D-Lys(Nic)-Leu-Lys(iPr)-Pro-D-Ala-NH$_2$ (5.37 gm) in DCM (20 mL) was treated with TFA (20 mL) for 25 minutes. The reaction was quenched in a mixture of EtOAc (265 mL), ACN (60 mL) and 17% K$_2$CO$_3$ (340 mL), the layers were separated, and the aqueous layer was extracted with EtOAc (120 mL). The organic layers were combined, washed with 17% K$_2$CO$_3$ (100 mL) and 1% NaCl (2×50 mL, with 0.25 mL concentrated NH$_4$OH), and evaporated in vacuo to dryness. The residue was dissolved in EtOAc (60 mL) and ACN (60 mL) and again evaporated in vacuo to dryness. The resulting oil was dissolved in NMP (18 mL), purged with nitrogen, and held for later use (Section B).

B. Coupling

A solution of Ac-D-2Nal-D-4ClPHe-D-3Pal-OH (2.40 gm), HOOBt (0.93 gm), CuCl$_2$.2H$_2$O (0.52 gm) and NMP (19 mL) was purged with nitrogen, then combined with the solution from Section A. The mixture was cooled to 0°–5° C. and 2,4,6-collidine (1.3 mL) and a solution of EDC.HCl (0.94 gm) in water 1.25 mL) was added and the mixture stirred at 0°–10° C. for 4 hours, followed by stirring overnight at ambient temperature under nitrogen. The reaction mixture was partitioned between EtOAc (300 mL), ACN (30 mL), 17% K$_2$CO$_3$ (60 mL) and 10% NH$_4$HCO$_3$ (150 mL). The layers were separated and the aqueous layer was extracted with EtOAc (200 mL). The organic layers were combined and washed with a mixture of 10% NH$_4$HCO$_3$ (140 mL) and 17% K$_2$CO$_3$ (70 mL), followed by 10% NH$_4$HCO$_3$ (180 mL) and by 17% K$_2$CO$_3$ (150 mL). The product was extracted into 20% citric acid (90 mL, then 60 mL), and the citric acid extracts combined and treated with activated carbon (2 gm) and celite (2 gm). The mixture was filtered through a bed of celite and filter bed washed with 20% citric acid (10 mL) and water (10 mL). The combined filtrates were covered with EtOAc (350 mL) and ACN (70 mL) and the pH adjusted to 11 with 33% K$_2$CO$_3$ (200 mL). The layers were separated and the organic layer was washed with water containing 0.5 mL NH$_4$OH(2×150 mL)), and evaporated in vacuo to dryness. The residue was treated with EtOAc (100 mL) and again evaporated in vacuo to dryness. The residue was dissolved in MeOH (4 mL) and EtOAc (16 mL) and this solution added to MTBE (360 mL) to precipitate the product. The solids were filtered, washed on the filter with MTBE (2×40 mL) and dried in vacuo to yield 5.90 gm of Ac-2Nal-D-4ClPHe-D-3Pal-Ser(Bzl)-NMeTyr(Cl$_2$Bzl)-D-Lys(Nic)-Leu-Lys(iPr)-Pro-D-Ala-NH$_2$. MS: (M+H)$^+$= 1782.

EXAMPLE 46

Ac-D-2Nal-D-4ClPhe-D-3Pal-Ser-NMeTyr-D-Lys(Nic)-Leu-Lys(iPr)-Pro-D-Ala-NH$_2$

A. Deprotection

A solution of Ac-D-2Nal-D-4ClPhe-D-3Pal-Ser(Bzl)-NMeTyr(Cl$_2$Bzl)-D-Lys(Nic)-Leu-Lys(iPr)-Pro-D-Ala-NH$_2$ (2.4 gm), 2,3,6-trimethylphenol (TMP, 4.0 gm) and TFA (14 mL) was stirred one hour at ambient temperature, then cooled to 0°–5° C. and trimethylsilyl trifluoromethane-sulfonate (TMSOTf, 4.0 mL) was added and the mixture stirred 75 minutes. The reaction was quenched in a mixture of MeOH (100 mL), water 150 mL) and conc. NH$_4$OH (14 mL) at 0°–5° C. The solution was then extracted with 20%(v/v) EtOAc/heptane (3×80 mL) and heptane (80 mL), and the pH of the aqueous phase adjusted to 6.9±0.1.

B. Ion-exchange Chromatography #1

The solution from above (Section A) was absorbed onto an ion exchange column of Amberlyte XAD-16 (125 gm), and the column washed with a 10% EDTA (pH adjusted to 6.9, 198 mL). The column was washed successively with water (260 mL), 10% NH$_4$OAc (825 mL), water (750 mL), 10% NH$_4$OAc (825 mL), water (825 mL) and 50% MeOH (500 mL). The product eluted with 0.1%HOAc/MeOH and the product-containing fractions combined and evaporated in vacuo to yield a yellow oil.

C. C-18 Reverse Phase Chromatography

The residue from above (Section B) was dissolved in MeOH (6 mL) and water (3 mL) and applied to a column of C-18 reverse phase resin (37 gm) which had been equilibrated with a 20/80/0.1 (v/v) ACN/water/TFA (20% ACN) mixture. The column was eluted successively with 20% ACN and 25% ACN mixtures. The product-containing fractions were combined and held for further processing (Section D).

D. Ion-Exchange Chromatography #2

The solution from above (Section C) was absorbed on a column Amberlyte CG-50 (40 gm), and the column washed successively with 50% MeOH (500 mL) and MeOH (500 mL). The product was eluted with a 4%(v/v) HOAc/MeOH solution and the product-containing fractions were combined and concentrated in vacuo to dryness. The residue was taken up in glacial acetic acid and lyophilized to yield 1.83 gm of Ac-D-2Nal-D-4ClPHe-D-3Pal-Ser-NMeTyr-D-Lys (Nic)-Leu-Lys(iPr)Pro-D-Ala-NH$_2$. MS: (M+H)$^+$=1534; amino acid analysis: 2Nal 1.0, 4ClPHe 0.9, 3Pal 1.0, Ser 0.9, NMeTyr 0.9, Lys (from Lys(Nic)) 1.0, Leu 1.0, Lys(iPr) 1.1., Pro 1.1., Ala 1.0.

We claim:

1. A process for preparing an LHRH antagonist having the structure Q-D2Nal$^1$-D4ClPHe$^2$-D3Pal$^3$-Ser$^4$-NMeTyr$^5$-DLys(Nic)$^6$-Leu$^7$-Lys(iPr)$^8$-Pro$^9$DAla$^{10}$NH$_2$ wherein Q is selected from the group consisting of N-acetyl and THF-Gly, comprising the steps of:

(a) fully deprotecting a first protected oligopeptide compound having the formula

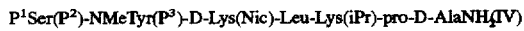

P$^1$Ser(P$^2$)-NMeTyr(P$^3$)-D-Lys(Nic)-Leu-Lys(iPr)-pro-D-AlaNH(IV)

wherein P$^1$ is an amino protecting group, and P$^2$ and P$^3$ are independently selected —OH protecting groups; and (b) coupling the unprotecting compound from step (a) with a second oligopeptide compound having the formula

Q-D-2Nal-D-4ClPhe-D-3Pal-OH        (III)

to produce said LHRH antagonist.

2. The process of claim 1 wherein said —OH protecting group is selected from the group consisting of allyl, cyclohexyl, methyl, methoxymethyl, methylthiomethyl, 2-methoxyethoxymethyl, bis(2-chloroethoxy)methyl, tetrahydropyranyl, tetrahydrothiopyranyl, tetrahydrofuranyl, 1-ethoxyethyl, t-butyl, benzyl, p-nitrobenzyl, 2,6-dichlorobenzyl, triphenylmethyl, trimethylsilyl, 9-fluorenylmethyl, isopropyldimethylsilyl, t-butyldimethylsilyl, t-butyldiphenylsilyl, triisopropylsilyl, acetate, trichloroacetate, phenacyl, phenoxyacetate, pivaloate, adamantoate, benzoate, mesitoate, allyl carbonate, methyl carbonate, 2,2,2-trichloroethyl carbonate, benzyl carbonate, p-nitrobenzyl carbonate, and 2-bromobenzyl carbonate.

3. The process of claim 1 wherein Q is THF-Gly.

4. The process of claim 1 wherein Q is N-acetyl.

5. The process of claim 1 wherein P$^2$ and P$^3$ are independently selected from benzyl and dichlorobenzyl.

6. The process of claim 1 further comprising the step of preparing compound IV by coupling a compound I having the formula

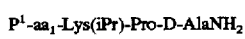

P$^1$-aa$_1$-Lys(iPr)-Pro-D-AlaNH$_2$ wherein aa$_1$ is absent or is Leu with a compound II having the formula

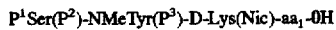

P$^1$Ser(P$^2$)-NMeTyr(P$^3$)-D-Lys(Nic)-aa$_1$-OH with the proviso that aa$_1$ is not simultaneously present in both compounds I and II.

7. The process of claim 6 further comprising the step of preparing compound I from P$^1$-Lys(P$^5$)-Pro-D-AlaNH$_2$ wherein P$^5$ is an amino protecting group orthogonal to P$^1$.

8. The process of claim 7 wherein P$^5$ is Fmoc, Boc or Cbz.

9. The process of claim 6 further comprising the step of preparing compound II from a compound B$_3$ having the formula P$^1$-Ser(P$^2$)-NMeTyr(P$^3$)-D-Lys(Nic)-aa$_1$-O-P$^4$ wherein P$^4$ is a carboxyl protecting group.

10. The process of claim 9 wherein P$^4$ is selected from the group consisting of 9-fluorenylmethyl, methoxymethyl, benzyl, p-nitrobenzyl, 2,2,2,-trichloroethyl, methylthiomethyl, benzyloxymethyl, t-butyl, methyl, ethyl, cyclohexyl, allyl and trimethylsilyl.

11. The process of claim 10 wherein P$^4$ is allyl or benzyl.

12. The process of claim 1 further comprising the step of preparing compound III from a compound C$_3$ having the formula Q-D-2Nal-D-4ClPHe-D-3Pal-O-P$^4$ wherein P$^4$ is a carboxyl protecting group as defined above.

13. The process of claim 12 wherein Q is THF-Gly.

14. The process of claim 13 further comprising the step of preparing compound C$_3$ by first reacting THF-Gly-OH with P$^1$-D-2Nal-D-4ClPhe-D-3Pal-O-P$^4$.

15. The process of claim 14 further comprising the step of preparing THF-Gly-OH from THF-Gly-O-P$^4$.

16. The process of claim 15 further comprising the step of preparing THF-Gly-O-P$^4$ by reacting the dicyclohexylamine salt of tetrahydrofuroic acid with the p-toluenesulfonic acid salt of Gly-O-P$^4$ and then hydrogenating the resulting product.

17. The process of claim 12 wherein Q is N-acetyl.

18. The process of claim 1 wherein P$^1$ is selected from the group consisting of tert-butyloxycarbonyl, benzyloxycarbonyl, biphenylisopropyloxycarbonyl, t-amyloxycarbonyl, isobornyloxycarbonyl, (alpha,alpha)-dimethyl-3,5-dimethoxybenzyl-oxycarbonyl, o-nitrophenylsulfenyl, 2-cyano-t-butyloxycarbonyl, and 9-fluorenylmethyloxycarbonyl.

* * * * *

UNITED STATES PATENT AND TRADEMARK OFFICE
CERTIFICATE OF CORRECTION

PATENT NO. : 5,710,247
DATED : January 20, 1998
INVENTOR(S) : Funk et al.

It is certified that error appears in the above-identified patent and that said Letters Patent is hereby corrected as shown below:

Column 2, line 5, change "Nal¹D" to --Nal¹-D--.

Column 41, line 49, change "pro" to --Pro--.

Column 41, line 49, change "AlaNH$_2$(IV)" to --AlaNH$_{2(IV)}$--.

Column 42, line 20, change "1I" to --II--.

Signed and Sealed this

Ninth Day of June, 1998

BRUCE LEHMAN

Attest:

Attesting Officer     *Commissioner of Patents and Trademarks*